(12) United States Patent
Kimoto et al.

(10) Patent No.: US 7,596,359 B2
(45) Date of Patent: Sep. 29, 2009

(54) RECEIVING APPARATUS, TRANSMITTING APPARATUS AND TRANSMITTING/RECEIVING SYSTEM

(75) Inventors: Seiichiro Kimoto, Tokyo (JP); Toshiaki Shigemori, Tokyo (JP); Ayako Nagase, Tokyo (JP); Manabu Fujita, Tokyo (JP); Akira Matsui, Tokyo (JP); Kazutaka Nakatsuchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 566 days.

(21) Appl. No.: 11/483,355

(22) Filed: Jul. 7, 2006

(65) Prior Publication Data

US 2006/0264734 A1 Nov. 23, 2006

Related U.S. Application Data

(63) Continuation of application No. PCT/JP2005/000115, filed on Jan. 7, 2005.

(30) Foreign Application Priority Data

| Jan. 7, 2004 | (JP) | 2004-002423 |
| Feb. 3, 2004 | (JP) | 2004-026875 |
| Mar. 4, 2004 | (JP) | 2004-061277 |
| Mar. 12, 2004 | (JP) | 2004-071579 |
| Mar. 12, 2004 | (JP) | 2004-071580 |
| Mar. 12, 2004 | (JP) | 2004-071581 |

(51) Int. Cl.
*H04B 17/02* (2006.01)
*A61B 1/04* (2006.01)
*A61B 1/00* (2006.01)

(52) U.S. Cl. ............ 455/137; 455/140; 348/55; 600/101

(58) Field of Classification Search ......... 455/39, 455/41.2, 562.1, 575.7, 69, 101, 132, 140, 455/137; 348/42, 45; 600/486, 101
See application file for complete search history.

(56) References Cited

U.S. PATENT DOCUMENTS

| 5,241,701 A |   | 8/1993 | Andoh |
| 5,243,416 A | * | 9/1993 | Nakazawa ............ 348/74 |
| 5,258,834 A | * | 11/1993 | Tsuji et al. ............ 348/71 |
| 5,303,396 A |   | 4/1994 | Ooyagi et al. |

(Continued)

FOREIGN PATENT DOCUMENTS

JP 61-109331 5/1986

(Continued)

*Primary Examiner*—Sonny Trinh
(74) *Attorney, Agent, or Firm*—Scully, Scott, Murphy & Presser, P.C.

(57) ABSTRACT

A receiving apparatus is for selecting and receiving a radio signal in a frame structure having an information body part including at least information body and an additional part including information for receiving field intensity measurement by using a plurality of antennas. The apparatus includes a controller that measures a receiving field intensity of not a first antenna which has received the information body in a transmission period of the additional part in a current frame but a second antenna, and measures a receiving field intensity of the first antenna in a transmission period of the information body part in the current frame, and if the receiving field intensity of the second antenna exceeds the receiving field intensity of the first antenna, selects and changes to the second antenna as the first antenna of a next frame.

13 Claims, 32 Drawing Sheets

U.S. PATENT DOCUMENTS

| | | |
|---|---|---|
| 5,335,010 A | 8/1994 | Lindemeier et al. |
| 5,604,531 A | 2/1997 | Iddan et al. |
| 6,120,435 A * | 9/2000 | Eino .......................... 600/118 |
| 6,154,248 A * | 11/2000 | Ozawa et al. ................. 348/65 |
| 6,292,516 B1 | 9/2001 | Petsko et al. |
| 6,904,308 B2 * | 6/2005 | Frisch et al. ................. 600/424 |
| 2001/0002842 A1 * | 6/2001 | Ozawa ........................ 348/45 |
| 2002/0173718 A1 | 11/2002 | Frisch et al. |
| 2003/0085994 A1 | 5/2003 | Fujita et al. |

FOREIGN PATENT DOCUMENTS

| | | |
|---|---|---|
| JP | 05-259950 | 10/1993 |
| JP | HEI 09-321678 | 12/1997 |
| JP | 2001-127680 | 5/2001 |
| JP | 2003-19111 | 1/2003 |
| JP | 2003-135389 | 5/2003 |
| JP | 2003-309501 | 10/2003 |

* cited by examiner

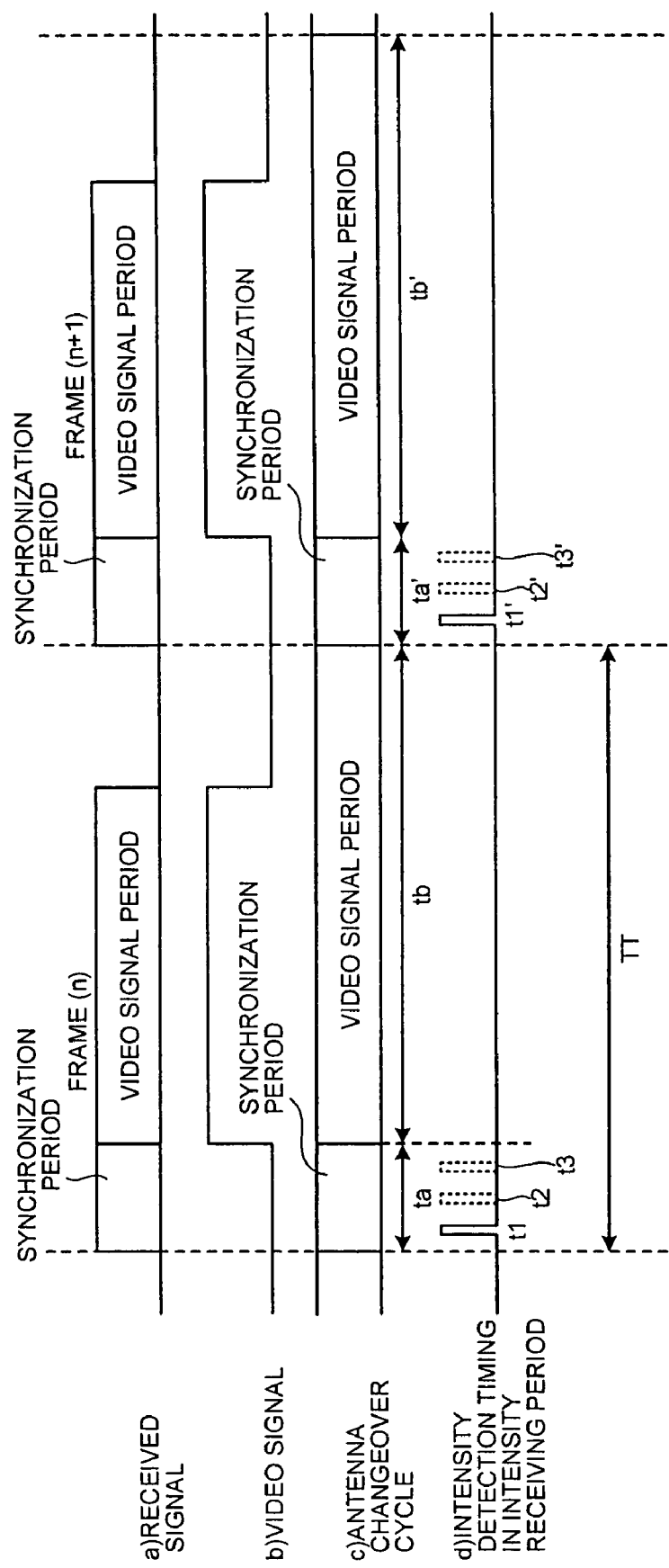

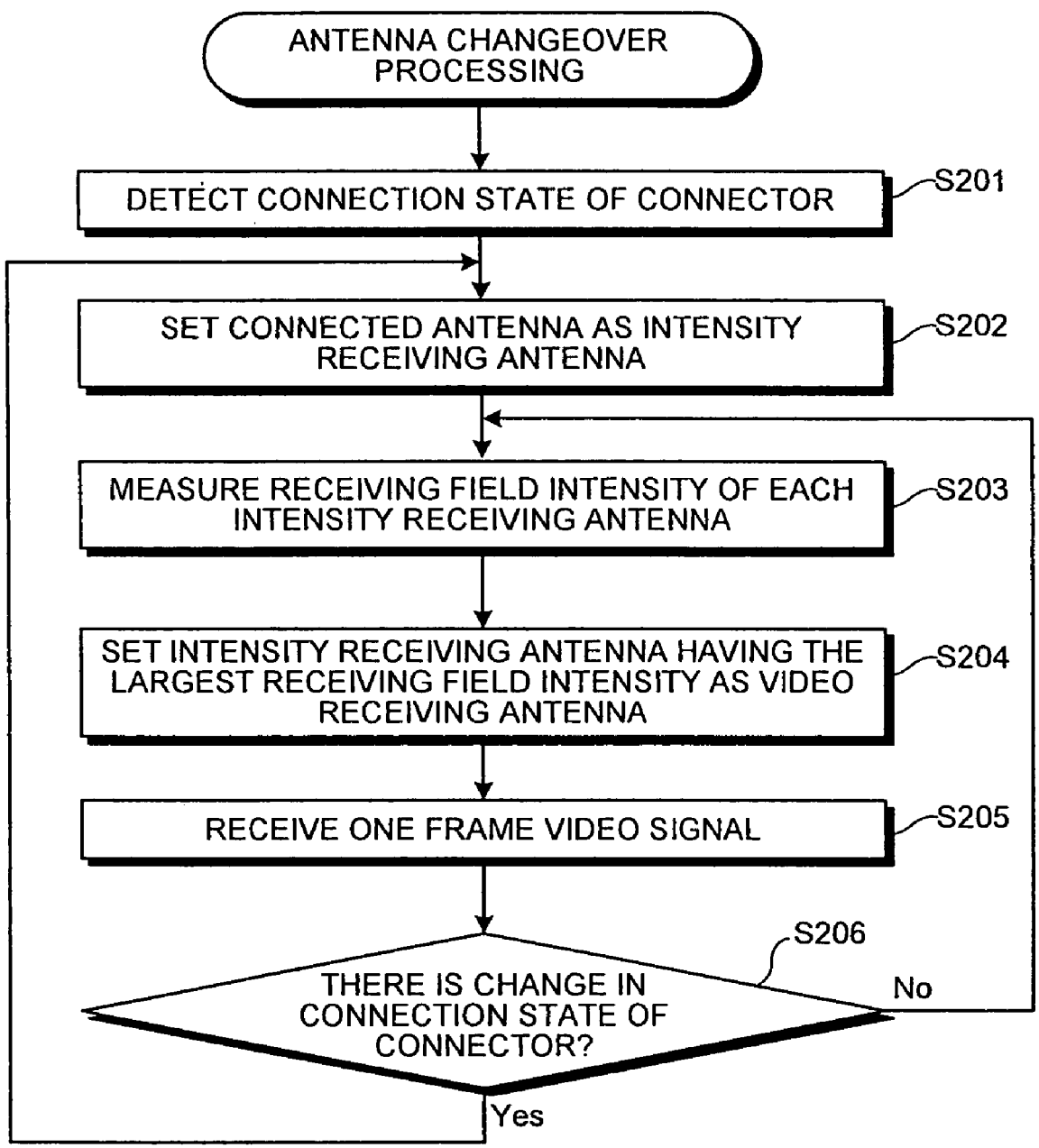

RECEIVING APPARATUS, TRANSMITTING APPARATUS AND TRANSMITTING/RECEIVING SYSTEM

CROSS-REFERENCE TO RELATED APPLICATIONS

This application is a continuation of PCT international application Ser. No. PCT/JP2005/000115 filed Jan. 7, 2005 which designates the United States, incorporated herein by reference, and which claims the benefit of priority from Japanese Patent Applications No. 2004-002423, filed Jan. 7, 2004; No. 2004-026875, filed Feb. 3, 2004; No. 2004-061277, filed Mar. 4, 2004; No. 2004-071579, filed Mar. 12, 2004; No. 2004-071580, filed Mar. 12, 2004; and No. 2004-071581, filed Mar. 12, 2004, all incorporated herein by reference.

BACKGROUND OF THE INVENTION

1. Field of the Invention

The present invention relates to a transmitting apparatus for transmitting an imaged video signal, a receiving apparatus for receiving the video signal by using a plurality of antennas, and a transmitting/receiving system having the transmitting apparatus and the receiving apparatus, and particularly to a transmitting/receiving system for receiving a radio video signal transmitted from a capsule endoscope within a subject by using a plurality of antennas outside the subject.

2. Description of the Related Art

In recent years, in the field of endoscope, there has appeared a swallow type capsule endoscope. This capsule endoscope is provided with an imaging function and a wireless communication function. The capsule endoscope has a function of, after being swallowed from the mouth of a patient for observation (inspection), moving and sequentially imaging inside the body cavity, for example, inside the organs such as stomach and small intestine according to their peristalses before being discharged from a human body.

While moving inside the body cavity, image data imaged inside the human body by the capsule endoscope is sequentially transmitted to the outside via wireless communication, and is accumulated in a memory provided in an external receiving apparatus. A patient brings the receiving apparatus comprising the wireless communication function and the memory function with him/her, and consequently the patient can freely act even in the period after he/she swallowed the capsule endoscope until it is discharged. Thereafter, a doctor or nurse can display the organs' images on a display based on the image data accumulated in the memory, thereby making a diagnosis.

Generally, the receiving apparatus is constituted so that a plurality of antennas for receiving a video signal transmitted from the capsule endoscope are distributed outside the human body and one antenna which is less erroneously receives the video signal is selected and changed for reception. Japanese Patent Application Laid-Open No. 2003-19111 describes a receiving apparatus which performs receiving changeover of a plurality of antennas arranged outside the human body and retrieves the position of the capsule endoscope inside the human body as a video signal originating source based on a field intensity received by each antenna.

SUMMARY OF THE INVENTION

A receiving apparatus according to one aspect of the present invention is for selecting and receiving a radio signal in a frame structure having an information body part including at least information body and an additional part including information for receiving field intensity measurement by using a plurality of antennas. The apparatus includes a controller that measures a receiving field intensity of not a first antenna which has received the information body in a transmission period of the additional part in a current frame but a second antenna, and measures a receiving field intensity of the first antenna in a transmission period of the information body part in the current frame, and if the receiving field intensity of the second antenna exceeds the receiving field intensity of the first antenna, selects and changes to the second antenna as the first antenna of a next frame.

A receiving apparatus according to another aspect of the present invention is for receiving a radio signal, transmitted from the inside of a subject, in a frame structure having a video signal part for transmitting at least a video signal and an additional part including information for receiving field intensity measurement by using a plurality of antennas provided outside the subject. The apparatus includes a changeover unit that selects and changes over the plurality of antennas; a field intensity measurement unit that measures a receiving field intensity of not a first antenna which has received the radio signal in a transmission period of the additional part in a current frame but a second antenna, and measures a receiving field intensity of the first antenna in a transmission period of the video signal part in the current frame; a selection controller that, when the receiving field intensity of the second antenna measured by the field intensity measurement unit exceeds the receiving field intensity of the first antenna, selects the second antenna as the first antenna of a next frame; and a changeover controller that sequentially changes over and connects an antenna other than the first antenna selected by the selection controller in a transmission period of the additional part of the next frame, and changes to and connects the selected first antenna in a transmission period of the video signal part.

A receiving apparatus according to still another aspect of the present invention is for selecting and receiving a radio signal in a frame structure having an information body part including at least information body and an additional part including information for receiving field intensity measurement by using a plurality of antennas. The apparatus includes a controller that measures receiving field intensities of more than two antennas in the additional part in a current frame, and selects and changes to an antenna having the largest receiving field intensity out of the more than two antennas as an antenna for receiving the information body part in a current frame.

A receiving apparatus according to still another aspect of the present invention is for selecting and receiving a radio signal in a frame structure having an information body part including at least information body and an additional part including information for receiving field intensity measurement by using a plurality of antennas. The apparatus includes a controller that compares a first receiving field intensity of an antenna which has received the information body in a previous frame with a second receiving field intensity being the largest receiving field intensity out of a result of measurement of receiving field intensities of more than two antennas other than the antenna in the additional part of a current frame, and selects and changes to the antenna having the larger receiving field intensity as an antenna for receiving the information body part in the current frame.

A receiving apparatus according to still another aspect of the present invention is for selecting and receiving a radio signal in a frame structure having an information body part including at least information body and an additional part including information for receiving field intensity measurement by using a plurality of antennas according to each receiving field intensity. Part of a synchronization period of the information body part is set at part or all of a receiving field intensity measurement period of the additional part to use a synchronization signal of the synchronization period as a signal for receiving field intensity measurement.

A receiving apparatus according to still another aspect of the present invention is for selecting and receiving a radio signal in a frame structure having an information body part including at least information body and an additional part including information for receiving field intensity measurement by using a plurality of antennas according to each receiving field intensity. Part of a synchronization period of the information body part is set at part or all of a receiving field intensity measurement period of the additional part to use a synchronization signal of the synchronization period as a signal for receiving field intensity measurement, and the antenna for receiving field measurement and the antenna for receiving the information body part are changed over in the synchronization period according to a measurement result of a receiving field intensity to each of the plurality of antennas.

A receiving apparatus according to still another aspect of the present invention is for receiving a video signal transmitted as a radio signal from a moving transmitting apparatus by using a plurality of antennas. The receiving apparatus includes a controller that sequentially changes over each antenna in a vertical blanking period of the video signal added with a dummy signal for receiving intensity measurement in the vertical blanking period to detect a receiving field intensity of the each antenna, and changes to an antenna having the largest receiving field intensity to cause the antenna to receive a video signal other than in the vertical blanking period.

A transmitting apparatus according to still another aspect of the present invention is for transmitting an imaged video signal as a radio signal to cause a receiving apparatus having a plurality of antennas to receive the video signal. A dummy signal for receiving field intensity measurement, which sequentially changes over each antenna of the receiving apparatus to receive the video signal and detects a receiving field intensity of each antenna, is added and transmitted in a vertical blanking period in the imaged video signal.

A transmitting/receiving system according to still another aspect of the present invention includes a transmitting apparatus for transmitting an imaged video signal as a radio signal and a receiving apparatus for receiving the video signal by using a plurality of antennas. The transmitting apparatus includes a dummy signal adder that adds and transmits a dummy signal in a vertical blanking period in the video signal. The receiving apparatus includes a controller that sequentially changes over each antenna in the vertical blanking period to detect a receiving field intensity of each antenna from the dummy signal, and changes to an antenna having the largest receiving field intensity to cause the antenna to receive a video signal other than in the vertical blanking period.

A receiving apparatus according to still another aspect of the present invention is for receiving a radio signal in a frame structure having an information body part including at least information body as a radio signal transmitted from a moving transmitting apparatus and an additional part including information for synchronization by using a plurality of antennas. The receiving apparatus includes a controller that sequentially changes over each antenna in a blank of the radio signal in which a dummy signal for receiving intensity measurement is added in the blank of the information body part whose arrangement position is previously determined to detect a receiving field intensity of each antenna, and changes to an antenna having the largest receiving field intensity to cause the antenna to receive a radio signal of the information body part other than in the blank.

A transmitting apparatus according to still another aspect of the present invention is for transmitting an imaged video signal as a radio signal to cause a receiving apparatus having a plurality of antennas to receive the video signal. Each antenna of the receiving apparatus is sequentially changed and received in a horizontal blanking period in the video signal to add and transmit a dummy signal for receiving field intensity measurement for detecting a receiving field intensity of each antenna.

A transmitting/receiving system according to still another aspect of the present invention includes a transmitting apparatus for transmitting an imaged video signal as a radio signal and a receiving apparatus for receiving the video signal by using a plurality of antennas. The transmitting apparatus includes a dummy signal adder that adds and transmits a dummy signal in a horizontal blanking period in the video signal. The receiving apparatus includes a controller that sequentially changes over each antenna in the horizontal blanking period to detect a receiving field intensity of the each antenna from the dummy signal, and changes to an antenna having the largest receiving field intensity to cause the antenna to receive a video signal other than in the horizontal blanking period.

A receiving apparatus according to still another aspect of the present invention is for receiving a radio signal in a frame structure having an information body part including at least information body as a radio signal transmitted from a moving transmitting apparatus and an additional part including information for receiving field intensity measurement. The receiving apparatus includes an antenna changeover unit that is connected to each antenna in correspondence to arrangement positions of the plurality of antennas and detects a connection state of each antenna to change over the connected antennas according to an instruction, and a controller that sequentially changes to an antenna whose connection has been detected by the antenna changeover unit on reception of the additional part to detect a receiving field intensity, and changes to an antenna having the largest receiving field intensity to cause the antenna to receive a radio signal of the information body part.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 29 is a time chart showing a receiving field intensity measurement processing for each frame by the receiving apparatus shown in FIG. 27;

FIG. 30 is a flowchart showing an antenna changeover processing procedure by a selection control unit of the receiving apparatus shown in FIG. 27;

DETAILED DESCRIPTION OF THE PREFERRED EMBODIMENTS

A wireless in-subject information acquiring system as the best mode for carrying out the present invention will be described below.

A wireless in-subject information acquiring system comprising a receiving apparatus according to an embodiment will be described. The wireless in-subject information acquiring system uses a capsule endoscope as one example of a in-subject introducing apparatus.

Figure 1:
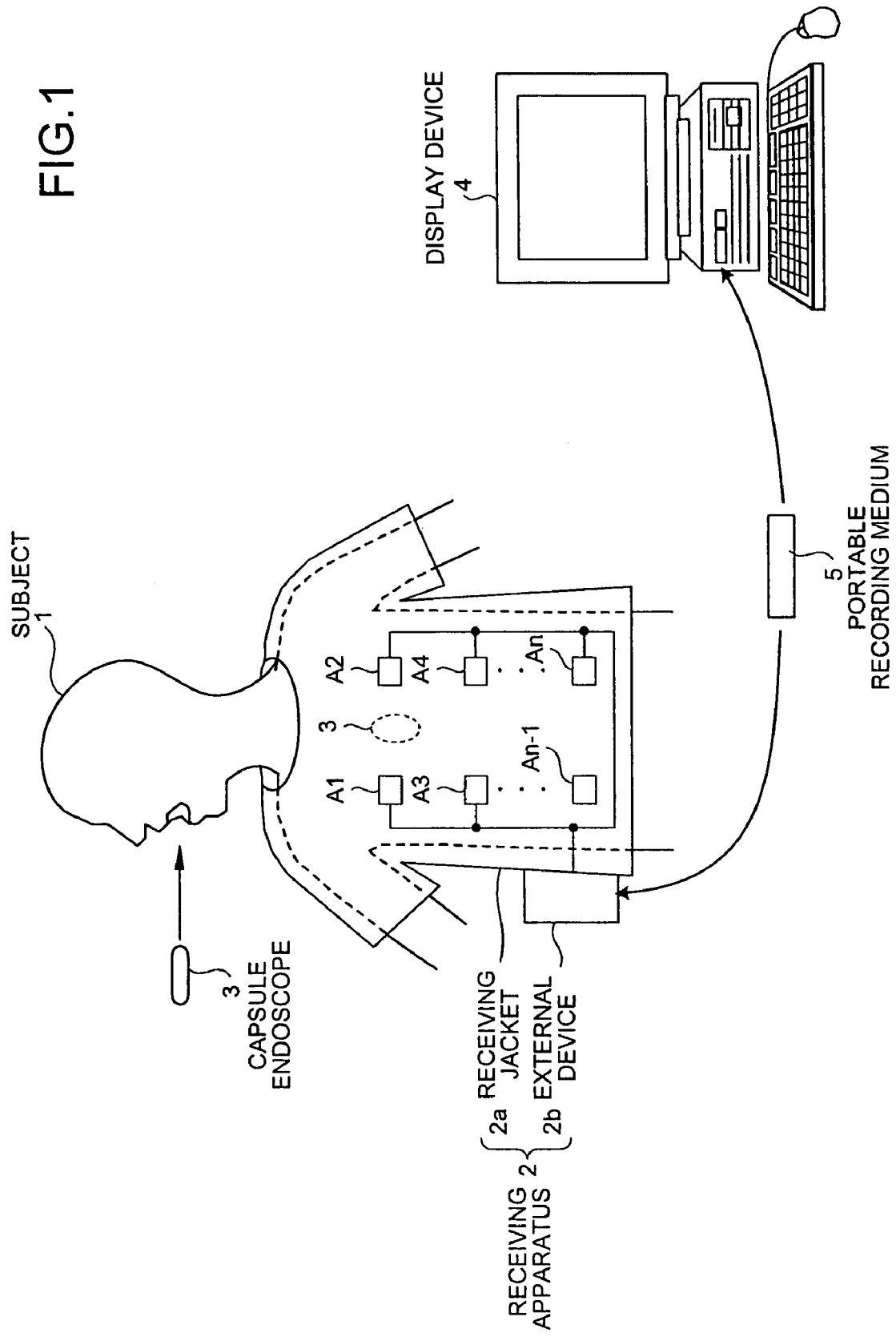
FIG. 1 is a schematic diagram showing the entire structure of a wireless in-subject information acquiring system including a receiving apparatus according to a first embodiment of the present invention.

FIG. 1 is a schematic diagram showing the entire structure of the wireless in-subject information acquiring system. As shown in FIG. 1, the wireless in-subject information acquiring system comprises a receiving apparatus 2 having a wireless receiving function, and a capsule endoscope (in-subject introducing apparatus) 3 introduced inside a subject 1 for imaging a body cavity image and transmitting data such as video signal to the receiving apparatus 2. Further, the wireless in-subject information acquiring system comprises a display device 4 for displaying the body cavity image based on the video signal received by the receiving apparatus 2, and a portable recording medium 5 for exchanging data between the receiving apparatus 2 and the display device 4. The receiving apparatus 2 comprises a receiving jacket 2a worn by the subject 1, and an external device 2b for performing a processing of a radio signal received via the receiving jacket 2a, or the like.

The display device 4 is directed for displaying the body cavity image imaged by the capsule endoscope 3, and has a structure such as work station for performing image display based on data obtained by the portable recording medium 5. Specifically, the display device 4 may be constituted to directly display an image by a CRT display, a liquid crystal display or the like, alternatively may be constituted to output an image to other medium such as printer.

The portable recording medium 5 has a structure to be detachable with respect to the external device 2b and the display device 4 and to be capable of outputting or recording information on being mounted on the both. Specifically, while the capsule endoscope 3 is moving inside the body cavity of the subject 1, the portable recording medium 5 is mounted on the external device 2b to record data transmitted from the capsule endoscope 3. Then, after the capsule endoscope 3 is discharged from the subject 1, that is, after the inside of the subject 1 finishes to be imaged, the portable recording medium 5 is taken out from the external device 2b to be mounted on the display device 4 so that the recorded data is read out by the display device 4. The data exchange between the external device 2b and the display device 4 is performed by the portable recording medium 5 such as compact flash (registered trademark) memory so that the subject 1 can more freely act while his/her body cavity is being imaged than when the external device 2b and the display device 4 are wire-connected, which contributes to a reduction in time for exchanging data with the display device 4. Here, the data exchange between the external device 2b and the display device 4 uses the portable recording medium 5, but it is limited thereto, and it may be constituted to use other recording apparatus incorporated in the external device 2b to be wired- or wirelessly connected for data exchange with the display device 4.

Figure 2:
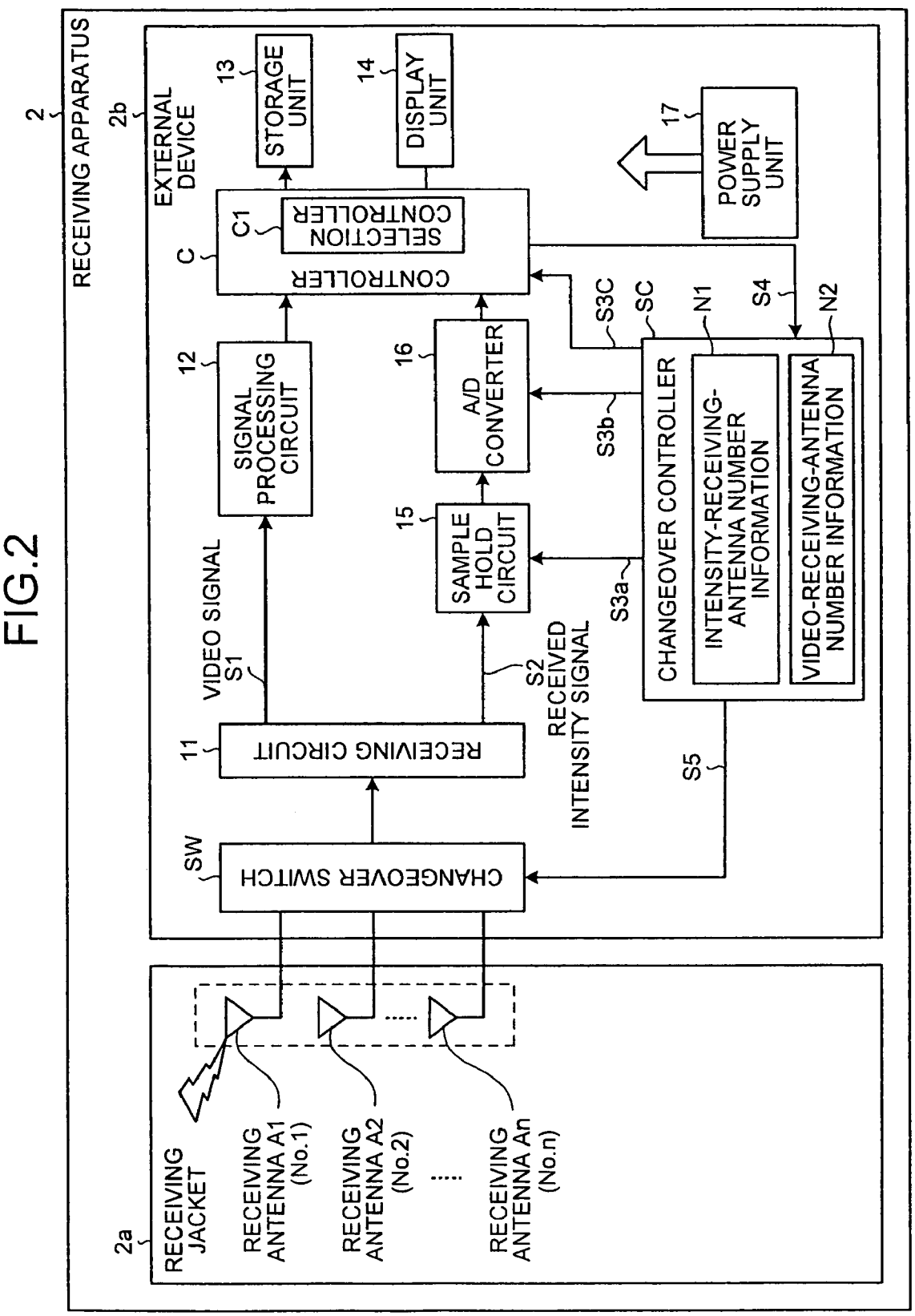
FIG. 2 is a block diagram showing a structure of the receiving apparatus shown in FIG. 1.

The receiving apparatus 2 will be described with reference to FIG. 2. The receiving apparatus 2 also has a function of receiving body cavity image data wirelessly transmitted from the capsule endoscope 3. FIG. 2 is a block diagram schematically showing the structure of the receiving apparatus 2. As shown in FIG. 2, the receiving apparatus 2 has a shape capable of being worn by the subject 1, and comprises the receiving jacket 2a having receiving antennas A1 to An, and the external device 2b for performing a processing for received radio signal, and the like. The respective receiving antennas A1 to An may be provided in the receiving jacket 2a to be directly attached to the outer surface of the subject, or may be detachable with respect to the receiving jacket 2a.

The external device 2b has a function of performing a processing for radio signal transmitted from the capsule endoscope 3. Specifically, the external device 2b, as shown in FIG. 2, has changeover switches SW for performing connection changeover of the receiving antennas A1 to An, and a receiving circuit 11 connected to the rear stage of the changeover switches SW for amplifying and demodulating a radio signal from the receiving antenna A1 to An changeover-connected by the changeover switch SW, and further the rear stage of the receiving circuit 11 is connected with a signal processing circuit 12 and a sample hold circuit 15. An A/D converter 16 is further connected to the rear stage of the sample hold circuit 15. A controller C has a selection controller C1 to connect a storage unit 13, a display unit 14 and a changeover controller SC corresponding to the signal processing circuit 12, the A/D converter 16 and the portable recording medium 5. The changeover controller SC has intensity-receiving-antenna number information N1 and video-receiving-antenna number information N2 to make changeover instruction of the changeover switches SW based on the number information and to instruct the processing timing of the sample hold circuit 15, the A/D converter 16 and the selection controller C1. A power supply unit 17 performs power supply to each unit described above, and is realized by a battery, for example.

The changeover switch SW of the external device 2b selectively changes over any one of the receiving antennas A1 to An based on a changeover instruction from the changeover controller SC, and outputs a radio signal from the changed receiving antenna A1 to An to the receiving circuit 11. As described above, the receiving circuit 11 amplifies the radio signal and outputs a demodulated video signal S1 to the signal processing circuit 12, and outputs a received intensity signal S2 indicating a receiving field intensity of the amplified radio signal to the sample hold circuit 15. Video data processed by the signal processing circuit 12 is stored in the storage unit 13 by the controller C and displayed by the display unit 14 for output. A signal subjected to sample hold by the sample hold circuit 15 is converted into a digital signal by the A/D converter 16 to be fetched by the controller C, and the selection controller C1 of the controller C selects a receiving antenna having the largest receiving field intensity from among the receiving field intensities received in an intensity receiving period in a synchronization period described later as a receiving antenna for a video signal period and outputs it as a signal S4 which assumes a receiving antenna number for receiving in the intensity receiving period as the intensity-receiving-antenna number information N1 and a receiving antenna number for the video signal period as the video-receiving-antenna number information N2 to the changeover controller SC. The changeover controller SC holds the intensity-receiving-antenna number information N1 and the video-receiving-antenna number information N2 instructed by the selection controller C1, and outputs a signal S5 which instructs the changeover switch SW to select and connect the receiving antenna A1 to An corresponding to the intensity-receiving-antenna number information N1 during the intensity receiving period and instructs the changeover switch SW to select and connect the receiving antenna A1 to An corresponding to the video-receiving-antenna number information N2 during the video receiving period, and outputs a signal S3a which instructs a sample hold timing by the sample hold circuit 15, a signal S3b which instructs an A/D converting timing by the A/D converter 16, and a signal S3c which instructs a selection control timing by the selection controller C1.

Figure 3:
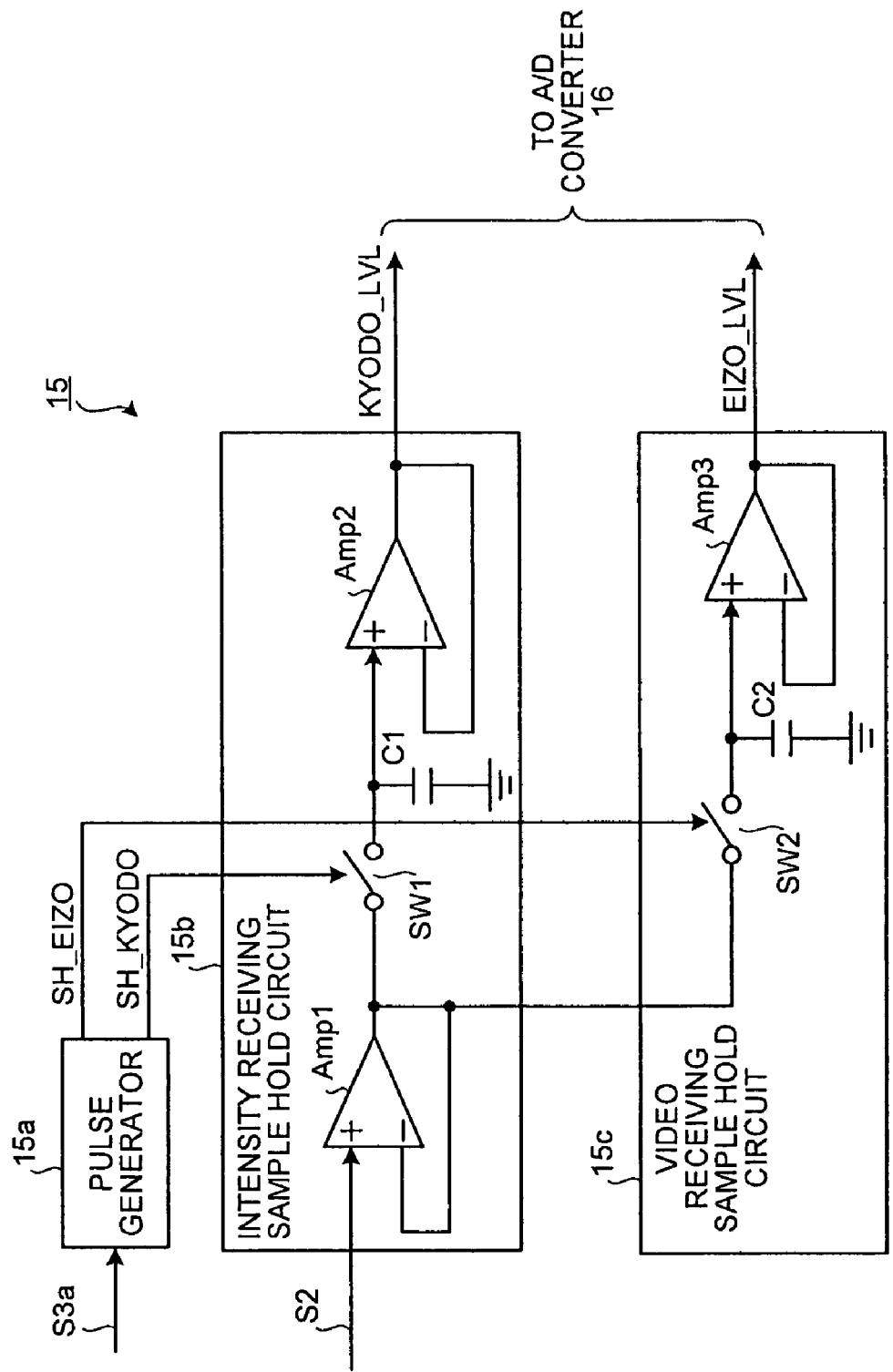
FIG. 3 is a block diagram showing a detailed structure of a sample hold circuit shown in FIG. 2.
Figure 4:
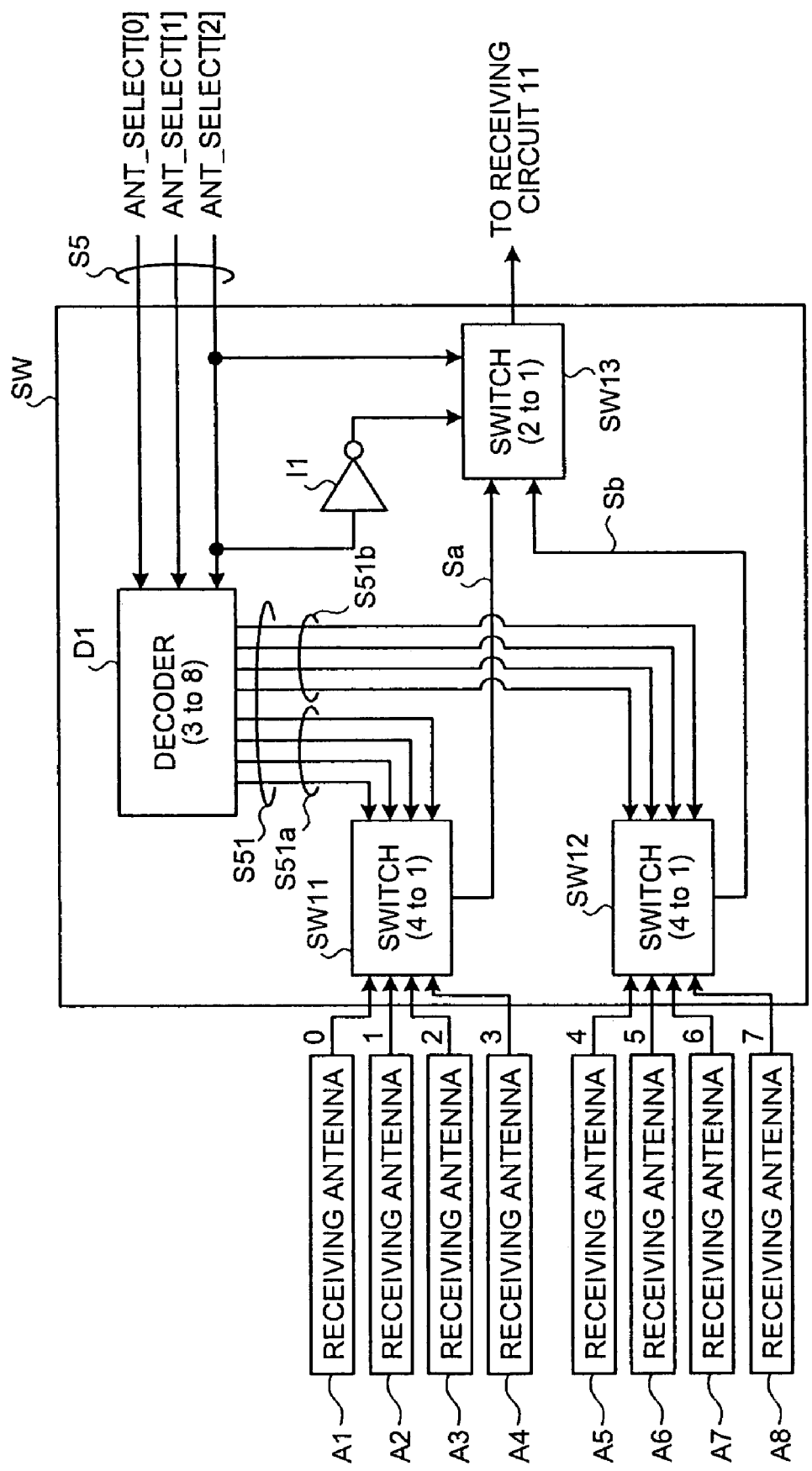
FIG. 4 is a block diagram showing a detailed structure of a changeover switch shown in FIG. 2.

Detailed structures of the sample hold circuit 15 and the changeover switch SW will be described with reference to FIG. 3 and FIG. 4. In FIG. 3, the sample hold circuit 15 has a pulse generator 15a for generating a sample hold pulse, an intensity receiving sample hold circuit 15b for sample-holding a receiving field intensity of the intensity receiving period, and a video receiving sample hold circuit 15c for sample-holding a receiving field intensity of the video receiving period.

The pulse generator 15a generates a pulse SH_KYODO and a pulse SH_EIZO which indicates a timing and a period of the sample hold by the intensity receiving sample hold circuit 15b based on the signal S3a input from the changeover controller SC. The pulse SH_KYODO and the pulse SH_EIZO are output to the switch SW1 of the intensity receiving sample hold circuit 15b and the switch SW2 of the video receiving sample hold circuit 15c, respectively.

The intensity receiving sample hold circuit 15b buffers the received intensity signal S2 input from the receiving circuit 11 by an amplifier Amp1. On the other hand, the switch SW1 enters the ON state during a period indicated from the timing indicated by the pulse SH_KYODO, charges are accumulated in a capacitor C1 to enter the OFF state so that the accumulated charges are buffered by an amplifier Amp2, and consequently the signal buffered by the amplifier Amp1 is output as a signal KYODO_LVL indicating the receiving field intensity of the intensity receiving period to the A/D converter 16.

On the other hand, the video receiving sample hold circuit 15c is input with the signal buffered by the amplifier Amp1 from the intensity receiving sample hold circuit 15b. The switch SW2 enters the ON state during a period indicated from a timing indicated by the pulse SH_EIZO, charges are accumulated in a capacitor C2 to enter the OFF state so that the accumulated charges are buffered by an amplifier Amp3, and consequently the signal buffered by the amplifier Amp1 is output as a signal EIZO_LVL indicating the receiving field intensity of the video signal period to the A/D converter 16.

A detailed structure of the changeover switch SW will now be described. In FIG. 4, the changeover switch SW has a decoder D1 for decoding a 3-bit signal S5 input from the changeover controller SC into an 8-bit signal S51, a switch SW11 connected to the receiving antennas A1 to A4 for selecting any one of them, a switch SW 12 connected to the receiving antennas A5 to A8 for selecting any one of them, a switch SW13 connected to the switches SW11 and SW 12 for selecting and outputting any one of signals Sa and Sb output from the switches SW11 and SW12, respectively, and an inverting circuit I1 for securing exclusive logic of the switch SW13 based on the highest bit input into the decoder.

The signal S5 is input into the decoder D1 as a 3-bit signal for selecting any one of the eight receiving antennas A1 to A8. This 3-bit signal S5 is a signal ANT_SELECT[0], signal ANT_SELECT[1] and signal ANT_SELECT[2], and the signal indicating the highest bit is the signal ANT_SELECT[2]. The decoder D1 decodes the 3-bit signal S5 into the 8-bit signal S51, outputs a lower 4-bit signal S51a to the switch SW11 for switching the smaller-numbered receiving antennas A1 to A4, and outputs a higher 4-bit signal S51b to the switch SW12 for switching the larger-numbered receiving antennas A5 to A8. The switches SW11 and SW12 select any one of the receiving antennas A1 to A8 according to the signals S51a and S51b, respectively. The switch SW13 selects any one of the signals Sa and Sb output from the switches SW11 and SW12 based on the highest bit signal ANT_SELECT[2]. When the switch 11 selects any one of the receiving antennas A1 to A4, the switch SW12 has not selected any one of the receiving antennas A5 to A8, but has input an inverting signal of the highest bit signal ANT_SELECT[2] by the inverting circuit I1 and performed exclusive logic in order to increase selection accuracy. A signal of the receiving antenna A1 to A8 finally selected by the switch SW13 is output to the receiving circuit 11. Here, the receiving antennas A1 to An has been described as the receiving antennas A1 to A8. The antenna number of each receiving antenna A1 to A8 is identification information unique to each receiving antennas and the numbers "1" to "8" are assumed as "0" to "7" for the sake of information processing.

Figure 5:
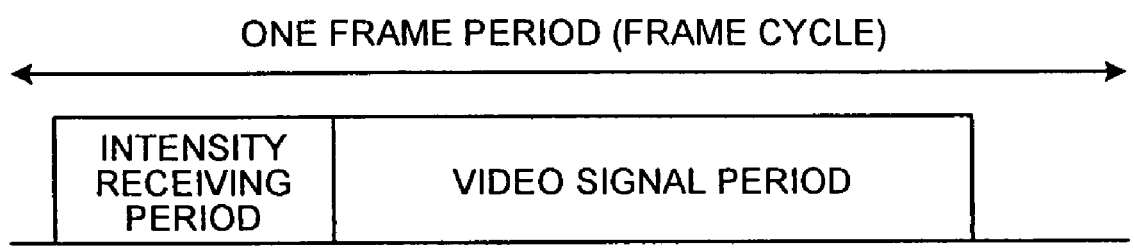
FIG. 5 is a diagram showing a frame format of a radio signal transmitted from a capsule endoscope shown in FIG. 1.

The intensity receiving period and video receiving period described above with reference to FIG. 5 and FIG. 6, that is, a frame structure of a radio signal will be described, and an outline of a processing of selecting and changing over the receiving antennas A1 to An will be described. A radio signal transmitted from the capsule endoscope 3 is transmitted in unit of frame, and this frame is constituted of the intensity receiving period and the video signal period as shown in FIG. 5. The intensity receiving period is a period corresponding to a preamble signal period for receiving adjustment. Further, the video signal period can contain a control signal necessary for receiving a video signal in addition to the video signal itself.

Figure 6:
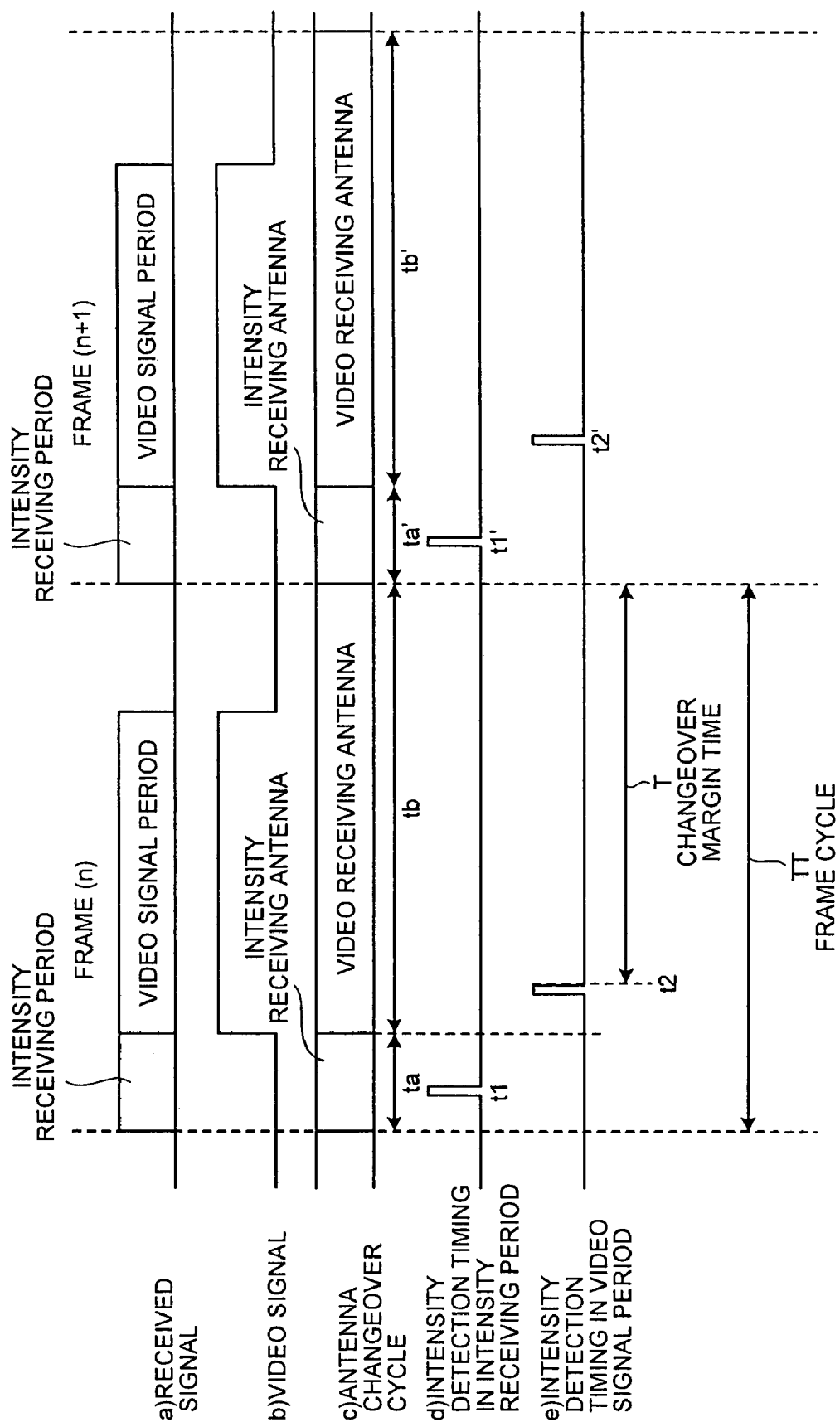
FIG. 6 is a time chart showing a receiving field intensity measurement processing for each frame by the receiving apparatus shown in FIG. 1.

Each frame may be transmitted as shown in FIG. 6 and a no-signal state may be between frames, or each frame may be continuously transmitted. A frame cycle TT for frame transmission is short in an imaging area of interest or in an area where the capsule endoscope 3 fast moves in consideration of effective utilization of the battery of the capsule endoscope 3, and the length of the frame cycle TT is flexibly adjusted.

As shown in FIG. 6, when the n-th frame (n) and the (n+1)-th frame (n+1) are sequentially transmitted, other receiving antenna (intensity receiving antenna) different from the receiving antenna (video receiving antenna) for receiving in the video signal period of the same frame (n) is changed over in a period ta corresponding to the intensity receiving period of the frame (n), and the video receiving antenna is changed over in a period tb including the video receiving period and a period to the start of the intensity receiving period of the next frame (n+1). Similarly, in a period ta' corresponding to the intensity receiving period of the frame (n+1), the intensity receiving antenna is changed over in the video signal period of the same frame (n+1) and the video receiving antenna is changed over in a period tb' including the video receiving period and a period to the start of the intensity receiving period of the next frame (n+2).

At timing t1 in the intensity receiving period of the frame (n), an intensity detection processing is performed by the sample hold circuit 15 and the A/D converter 16 and a result thereof is output to the selection controller C1. Similarly, at timing t2 in the video signal period of the frame (n), the intensity detection processing is performed by the sample hold circuit 15 and the A/D converter 16 and a result thereof is output to the selection controller C1. Therefore, a margin period to the antenna changeover processing of the next frame (n+1) is a changeover margin time T from timing t2 to the start of the intensity receiving period of the next frame (n+1). Thus, the timing t2 is set at an earlier point in the video signal period so that the changeover margin time T can be made long. Due to the long changeover margin time T, the sample hold circuit 15, the A/D converter 16, the selection changeover controller C1, the changeover controller SC and the changeover switch SW do not require high speed performance and can be realized using a simple circuit apparatus. The receiving field intensity of the receiving antenna for receiving the video signal is received and measured in the video signal period and does not require to be measured in the intensity receiving period so that the antenna does not require to be changed over at high speed. Further, this results in a changeover margin because the receiving field intensity of the self-video signal does not require to be measured when the receiving field intensities of a plurality of receiving antennas are measured in the intensity receiving period.

Figure 7:
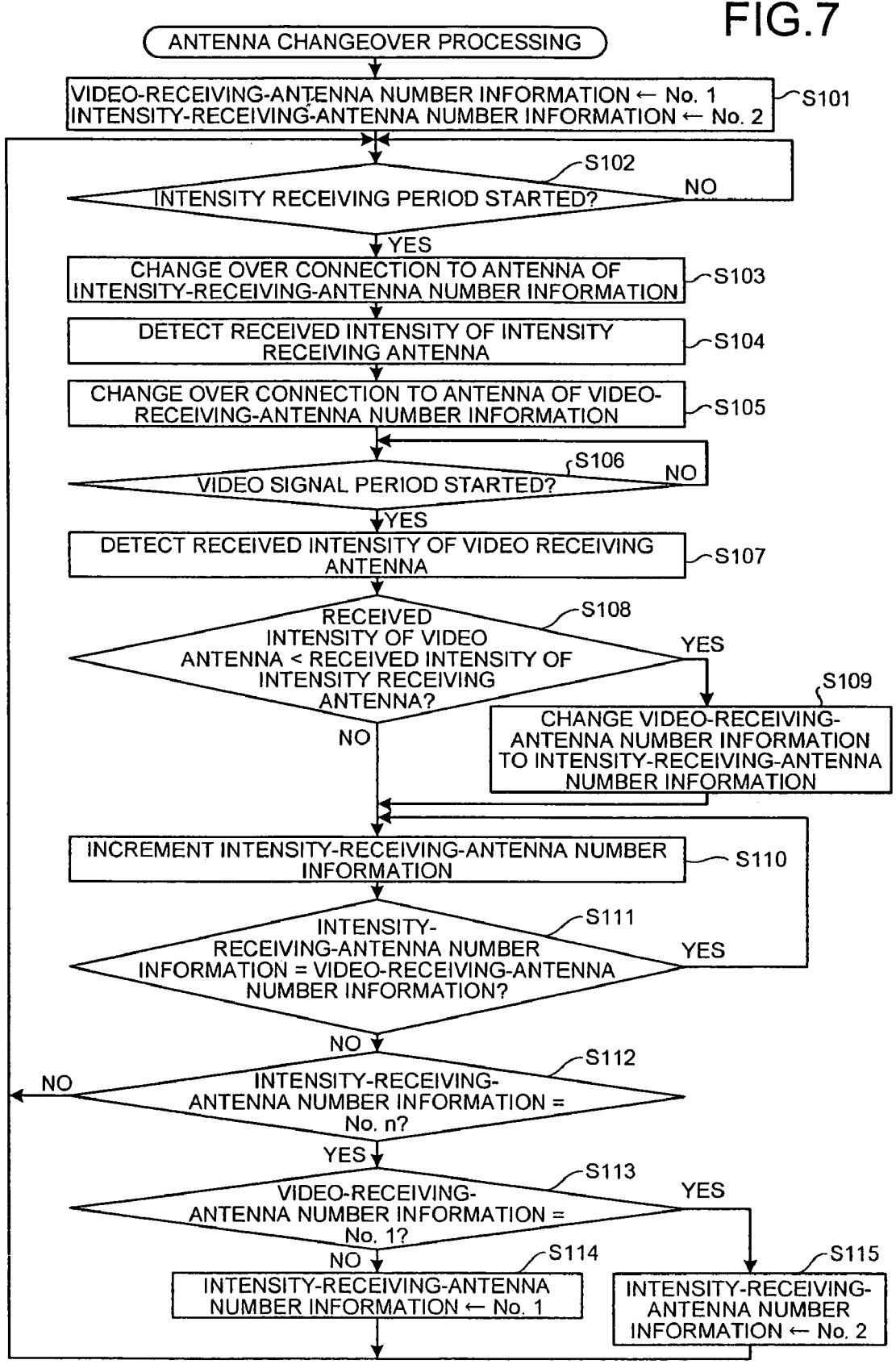
FIG. 7 is a flowchart showing an antenna changeover processing procedure by the receiving apparatus shown in FIG. 1.

An antenna changeover processing procedure will be described with reference to a flowchart shown in FIG. 7. The antenna changeover processing is performed by the selection controller C1 and the changeover controller SC. In FIG. 7, the selection controller C1 first sets, as initial setting, the video-receiving-antenna number information as the video receiving antenna number to be No. 1 and the intensity-receiving-antenna number information as the intensity receiving antenna number to be No. 2, and registers the same in the video-receiving-antenna number information N2 and the intensity-receiving-antenna number information N1 in the changeover controller SC (step S101). Here, No. 1 to No. n of the video-receiving-antenna number information and the intensity-receiving-antenna number information are the numbers corresponding to the receiving antennas A1 to An, respectively.

Thereafter, the changeover controller SC determines whether the intensity receiving period has started (step S102). If the intensity receiving period has started (step S102, YES), the changeover controller SC outputs an instruction of changing to the receiving antenna corresponding to the intensity-receiving-antenna number information registered in the intensity-receiving-antenna number information N1 to the changeover switch SW (step S103), and the changeover switch SW changes to the instructed receiving antenna. Thereafter, the changeover controller SC causes the sample hold circuit 15 and the A/D converter 16 to perform a processing of detecting the receiving field intensity of the intensity receiving antenna at timing t1 (step S104), and instructs the changeover switch SW to change to the receiving antenna registered in the video-receiving-antenna number information N2 at the start of the video receiving period (step S105) so that the changeover switch SW changes to the instructed receiving antenna. The changeover time in step S105 may not be at the start of the video signal period, or may be within the intensity receiving period if it is at the end of the field intensity measurement processing for the intensity receiving antenna.

Thereafter, the changeover controller SC determines whether the video signal period has started (step S106). The video signal period used here may be assumed as a period in which the video signal is transmitted if the control signal or the like is included in the video signal period. Thereafter, if the video signal period has started (Step S106, YES), the sample hold circuit 15 and the A/D converter 16 are caused to perform the processing of detecting the receiving field intensity of the intensity receiving antenna at timing t2 (step S107).

Thereafter, the selection controller C1 determines whether the receiving field intensity of the video receiving antenna received in the video signal period (video receiving antenna intensity) is smaller than the receiving field intensity of the intensity receiving antenna received in the intensity receiving period (intensity receiving antenna intensity) (step S108). If the video receiving antenna intensity is smaller than the intensity receiving antenna intensity (step S108, YES), the video-receiving-antenna number information is registered in the intensity-receiving-antenna number information N1 as the intensity-receiving-antenna number information (step S109), and the processing proceeds to step S110. On the other hand, if the video receiving antenna intensity is not smaller than the intensity receiving antenna intensity (step S108, NO), that is, when the video receiving antenna intensity exceeds the intensity receiving antenna intensity, the value of the intensity-receiving-antenna number information N1 is incremented as it is (step S110).

Thereafter, it is determined whether the value of the intensity-receiving-antenna number information coincides with the value of the video-receiving-antenna number information (step S111), if it coincides therewith (step S111, YES), the processing proceeds to step S110 to increment the value of the intensity-receiving-antenna number information, and if it does not coincides therewith (step S111, NO), it is further determined whether the intensity-receiving-antenna number information is No. n (step S112). If the intensity-receiving-antenna number information is not No. n (step S112, NO), the processing proceeds to step S102 to repeat the above processing, and if the intensity-receiving-antenna number information is No. n (step S112, YES), it is further determined whether the video-receiving-antenna number information is No. 1 (step S113). If the video-receiving-antenna number information is not No. 1 (step S113, NO), the intensity-receiving-antenna number information is set and registered to be No. 1 (step S114), and if the video-receiving-antenna number information is No. 1 (step S113, YES), the intensity-receiving-antenna number information is set and registered to be No. 2 (step S115), and then the processing proceeds to step S102 to repeat the above processing.

Since the first embodiment is constituted to measure the receiving field intensity of the video signal in the video signal period, to sequentially change to the receiving antenna other than the receiving antenna for receiving the video signal in the intensity receiving period to measure the receiving field intensity, and to change the receiving antenna changed in the intensity receiving period to the receiving antenna for the video receiving period when the receiving field intensity measured in the intensity receiving period exceeds the receiving field intensity measured in the video receiving period, the intensity receiving period can be reduced, a margin can be allowed in the time to change over the receiving antenna in the intensity receiving period, the intensity detection timing is made earlier in the video receiving period so that a time margin can be allowed in the antenna changeover setting between frames, and consequently high speed performance is not required for the structure on the receiving field intensity measurement, thereby achieving the simple structure.

A second embodiment according to the present invention will now be described. The second embodiment is constituted so that a peak hold circuit 18 is further provided between the receiving circuit 11 and the sample hold circuit 15 according to the first embodiment.

Figure 8:
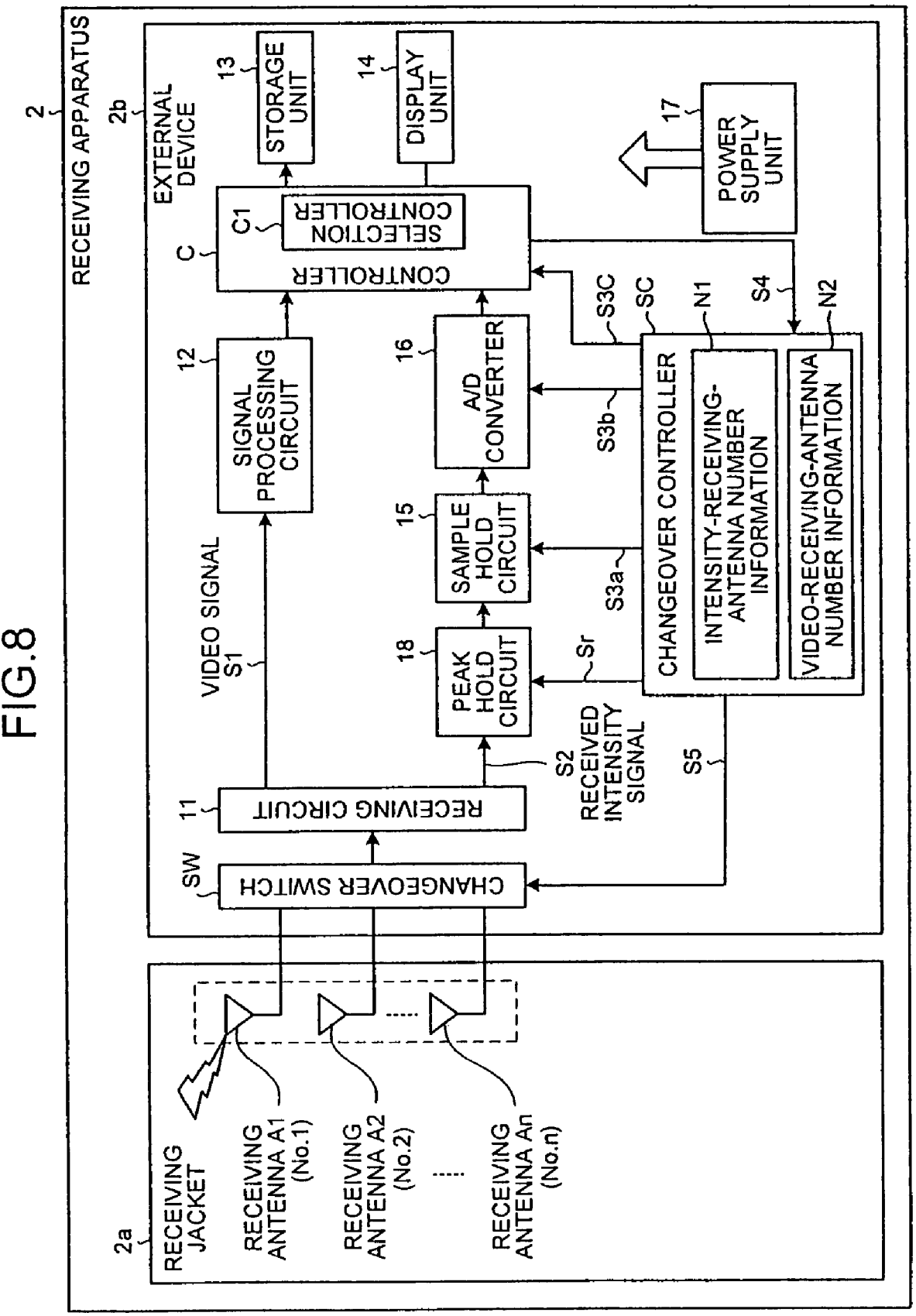
FIG. 8 is a block diagram showing a structure of a receiving apparatus according to a second embodiment of the present invention.

FIG. 8 is a block diagram showing a structure of a receiving apparatus according to the second embodiment of the present invention. As shown in FIG. 8, the receiving apparatus is provided with the peak hold circuit 18 and holds a peak value of the received intensity signal S2 output from the receiving circuit 11.

Figure 9:
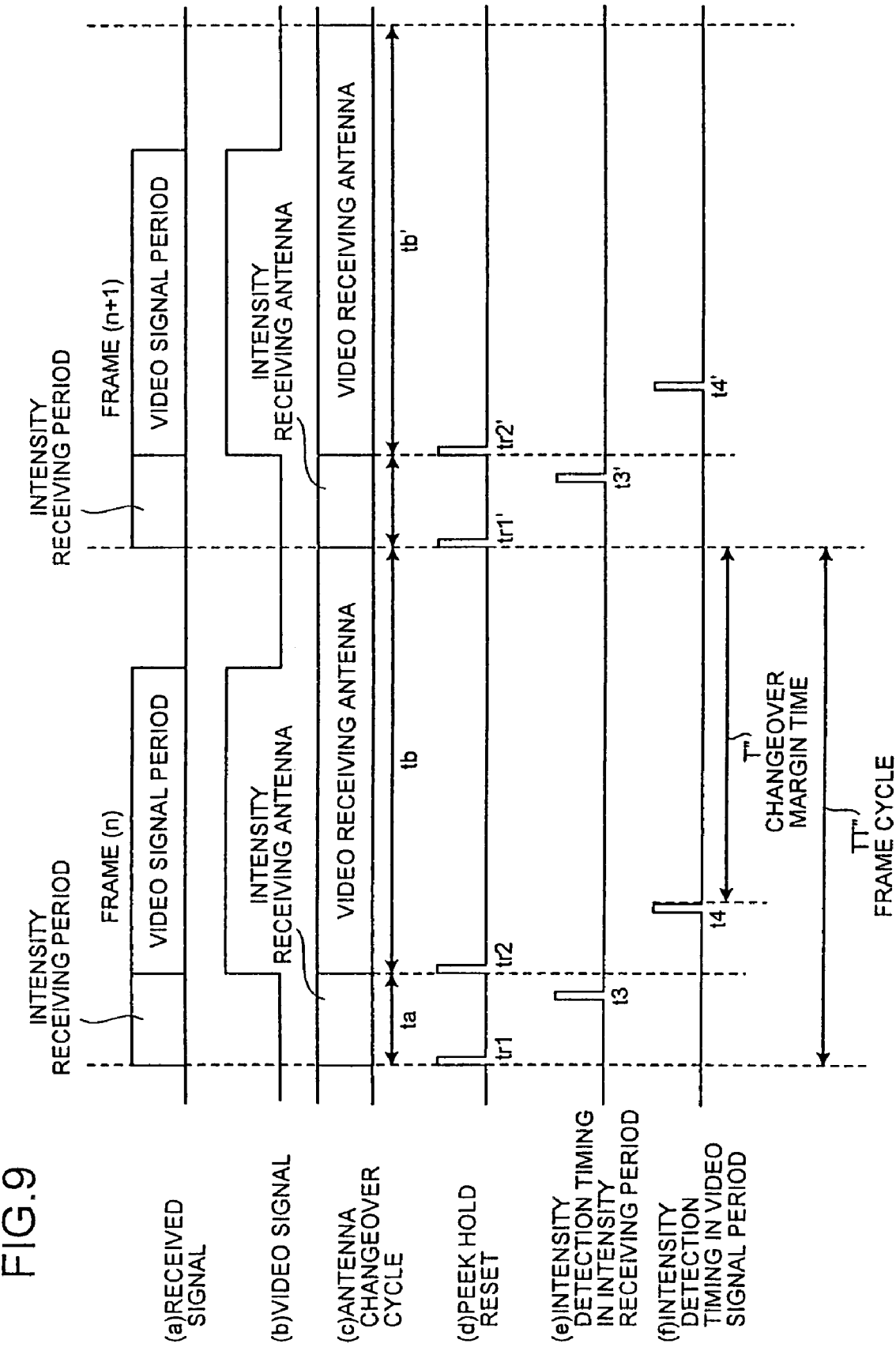
FIG. 9 is a time chart showing a receiving field intensity measurement processing for each frame by the receiving apparatus shown in FIG. 8.

Thus, as shown in FIG. 9, the changeover controller SC outputs a signal Sr to the peak hold circuit 18 at the start of the intensity receiving period and resets it at timing tr1. Thereafter, the changeover controller SC acquires a peak value held by the peak hold circuit 18 at detection timing t3 of the sample hold circuit 15, and again resets the peak hold circuit 18 at timing tr2 at the start of the video signal period. The sample hold circuit 15 acquires the peak value held by the peak hold circuit 18 at timing t4 after timing tr2. In other words, the sample hold circuit 15 can sample the peak value between timing tr1 and timing t3 and can sample the peak value between timing tr2 and timing tr4, thereby performing the receiving field intensity measurement with higher accuracy.

Figure 10:
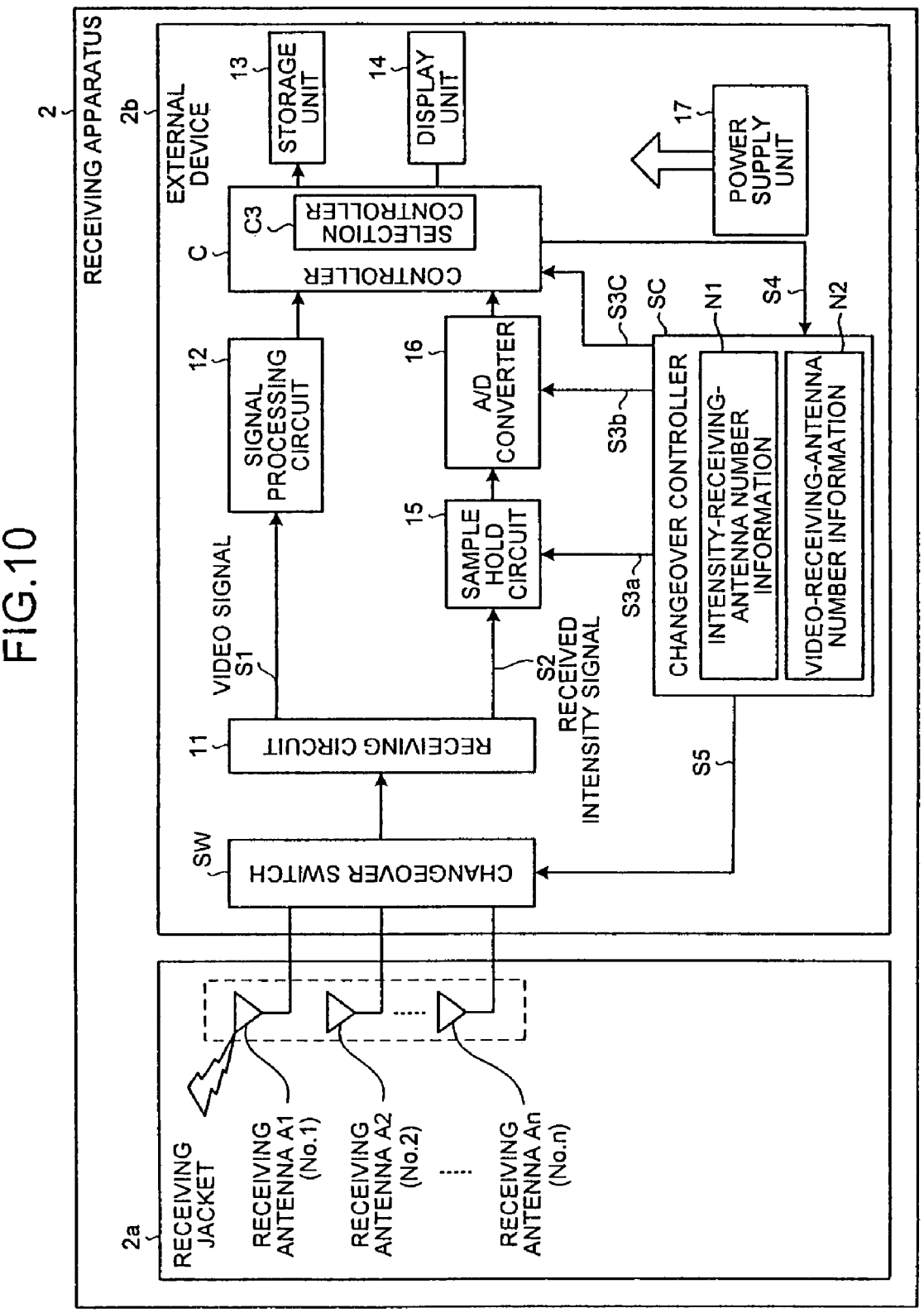
FIG. 10 is a block diagram showing a structure of a receiving apparatus according to a third embodiment of the present invention.

A third embodiment according to the present invention will now be described. The third embodiment is constituted so that the receiving field intensity measurement for all the receiving antennas is performed in the intensity receiving period to select a receiving antenna having the largest receiving field intensity as the video receiving antenna. FIG. 10 is a block diagram showing a structure of a receiving apparatus according to the third embodiment of the present invention. As shown in FIG. 10, the receiving apparatus is provided with a selection controller C3 instead of the selection controller C1. Other configurations are identical to those in the first embodiment and like numerals are denoted to like configurations.

Figure 11:
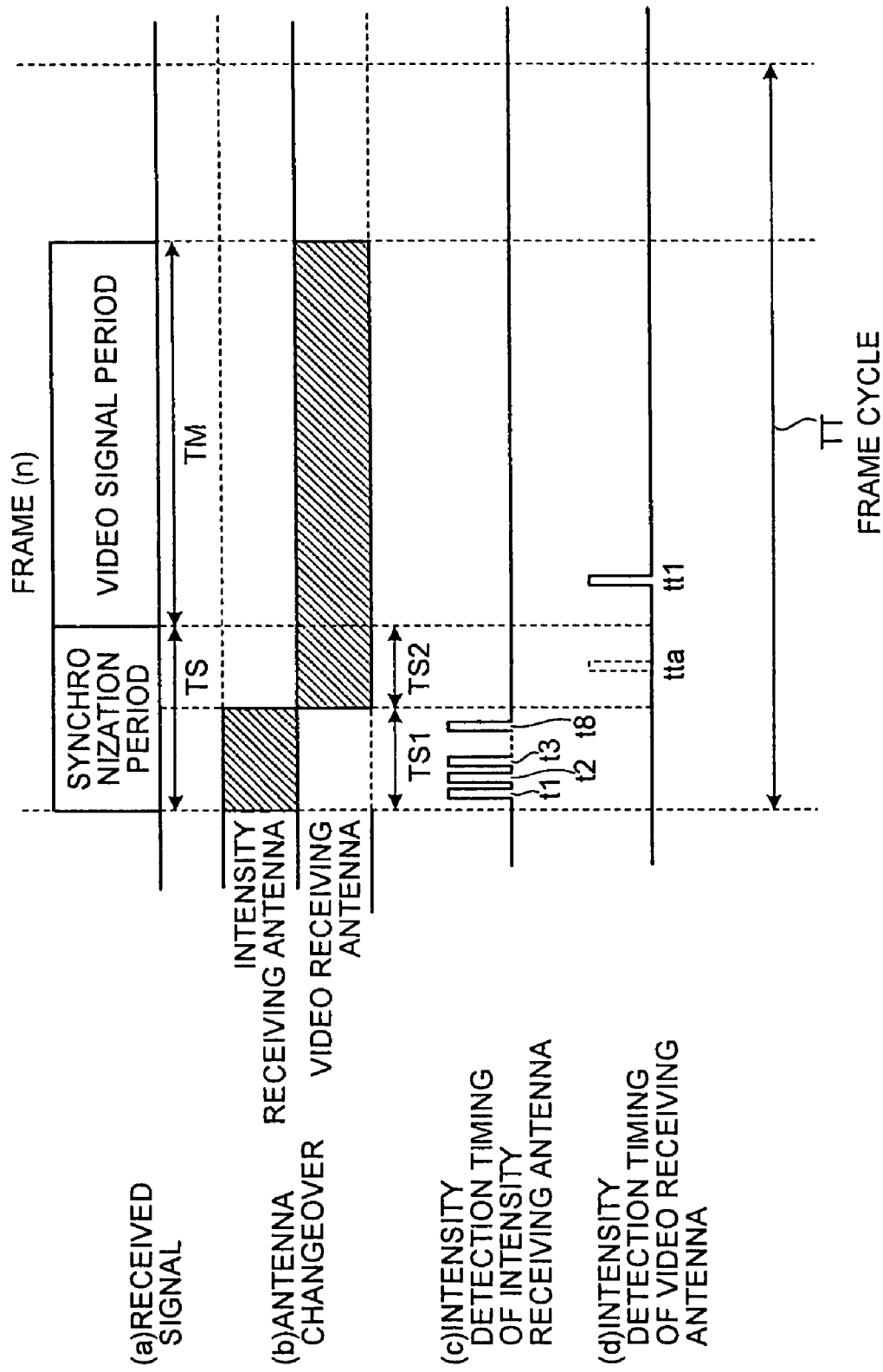
FIG. 11 is a timing chart for explaining an antenna changeover processing by the receiving apparatus shown in FIG. 10.

The intensity receiving period and video receiving period described above with reference to FIG. 11, that is, the frame structure of a radio signal will be described, and an outline of a processing of selecting and changing over the receiving antennas A1 to An will be described. A radio signal transmitted from the capsule endoscope 3 is transmitted in unit of frame and is constituted of the synchronization period and the video signal period as shown in FIG. 11. The synchronization period is a period corresponding to the preamble signal period for receiving adjustment. Further, the video signal period can contain a control signal necessary for receiving the video signal in addition to the video signal itself.

Each frame is transmitted as shown in FIG. 11 and a no-signal state may be between frames or each frame may be continuously transmitted. A frame cycle TT for frame transmission is short in an imaging area of interest or in an area where the capsule endoscope 3 fast moves in consideration of effective utilization of the battery of the capsule endoscope 3, and the length of the frame cycle TT is flexibly adjusted.

As shown in FIG. 11, the synchronization period TS in the n-th frame (n) has an intensity receiving period TS1 for selecting a receiving antenna having the largest receiving field intensity and a synchronization period TS2 for the video signal, and antenna changeover is performed between the intensity receiving period TS1 and the synchronization period TS2. Here, when the receiving antennas A1 to An are eight receiving antennas, the antenna changeover of all the receiving antennas A1 to A8 is performed in the intensity receiving period TS1 and the receiving field intensity measurement is performed at timings t1 to t8 within the period of each changed state. Peak hold pulses at timings t1 to t8 are generated by the pulse generator 15a.

When the receiving field intensity measurement for all the receiving antennas A1 to A8 is terminated, the selection controller C3 selects a receiving antenna having the largest receiving field intensity at the point and selects the receiving antenna as the video receiving antenna in the synchronization period TS2 and video signal period TM. The receiving field intensity measurement by the video receiving antenna is performed in the video signal period TM or synchronization period TS2 at timing tt1 or timing tta. The receiving field intensity measurement by the video receiving antenna may not be performed if not needed. It is performed for receiving state confirmation in the third embodiment.

Since the third embodiment is constituted so that the receiving field intensity measurement for all the receiving antennas is performed in the intensity receiving period TS1 to select a receiving antenna having the largest receiving field intensity as the video receiving antenna, less video signals are transmitted in vain and a small number of video signals can be securely received. Consequently, power saving of the capsule endoscope 3 can be promoted.

A fourth embodiment according to the present invention will now be described. The forth embodiment is constituted so that the result of the receiving field intensity measurement by the video receiving antenna is effectively utilized to select and process the video receiving antenna.

Figure 12:
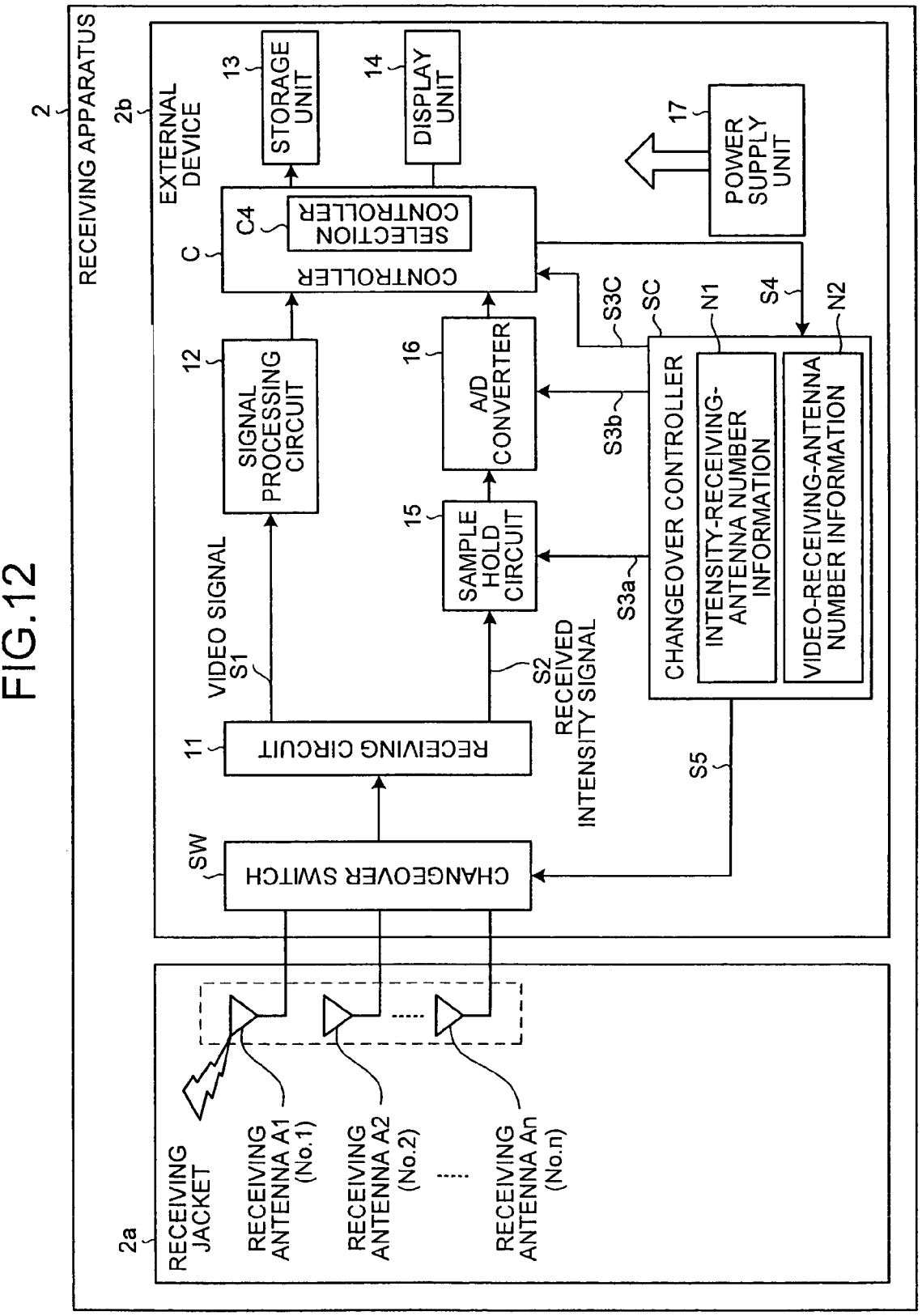
FIG. 12 is a block diagram showing a structure of a receiving apparatus according to a fourth embodiment of the present invention.

FIG. 12 is a block diagram showing a structure of a receiving apparatus according to the fourth embodiment of the present invention. As shown in FIG. 12, the receiving apparatus is provided with a selection controller C4 instead of the selection controller C1. Other configurations are identical to those in the first embodiment and like numerals are denoted to like configurations.

Figure 13:
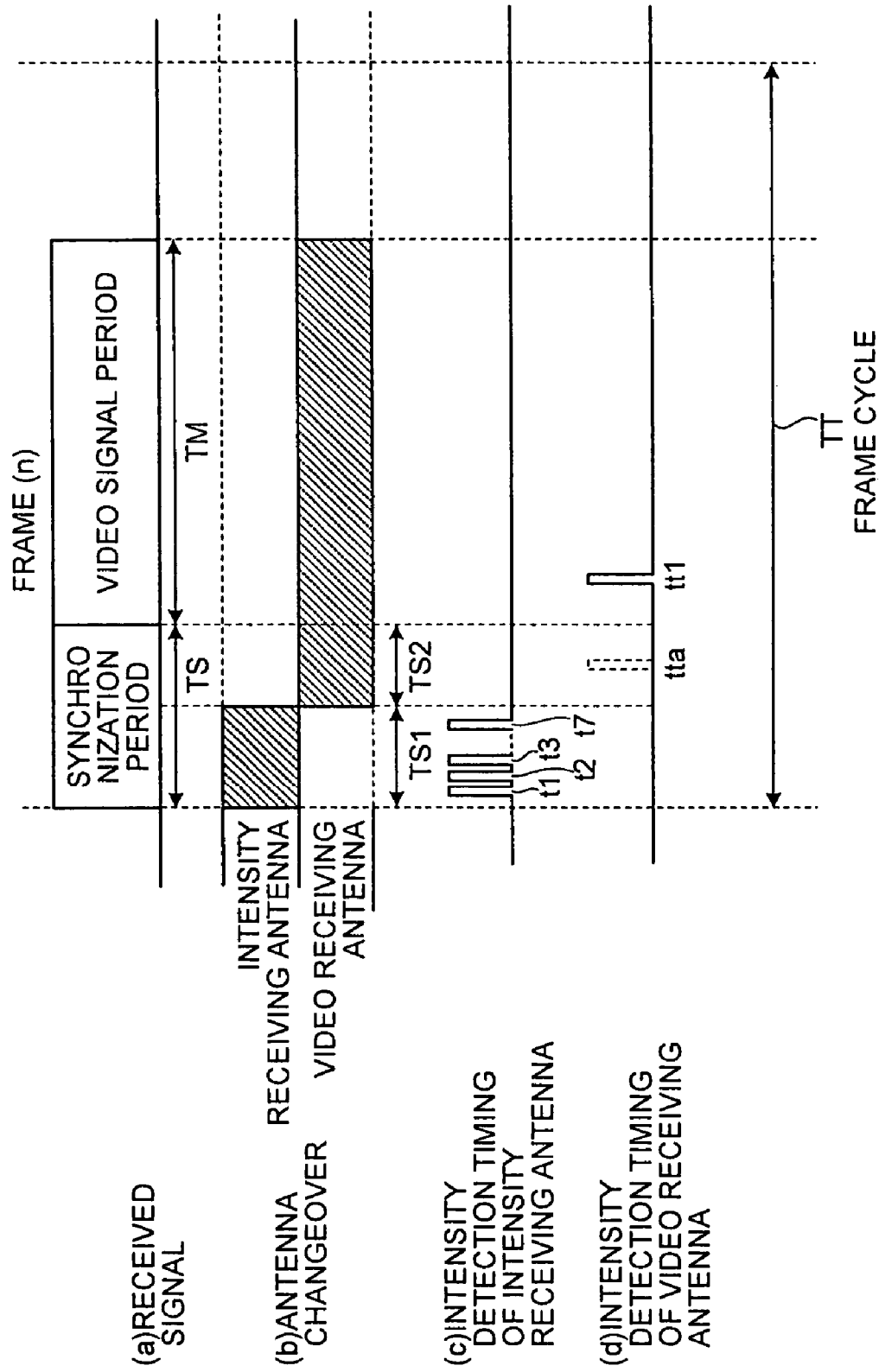
FIG. 13 is a timing chart for explaining an antenna changeover processing by the receiving apparatus shown in FIG. 12.

The selection controller C4, as shown in FIG. 13, excludes the receiving antenna selected as the video signal antenna in the frame (n−1) from the intensity receiving antennas, and assumes the remaining seven receiving antennas as the intensity receiving antennas to cause them to perform the receiving field intensity measurement for each receiving antenna in the intensity receiving period TS1. The selection controller C4 determines the receiving antenna having the largest receiving field intensity in the intensity receiving period TS1, and compares the receiving field intensity of the determined receiving antenna with the receiving field intensity of the video receiving antenna in the frame (n−1) to select the receiving antenna having the higher receiving field intensity as the video receiving antenna for the frame (n). The selected video receiving antenna measures the receiving field intensity in the synchronization period TS2 or video signal period TM and a result thereof is used to determine the video receiving antenna for the frame (n+1).

Since the fourth embodiment is constituted so that the receiving field intensity of the video receiving antenna is measured in the previous video signal period TM having a time margin and only the receiving antenna is excluded from the intensity receiving antennas in the intensity receiving period TS1 to select a receiving antenna having the largest receiving field intensity from among the receiving field intensities as the video receiving antenna, secure video signals can be received in a short time.

Although all the receiving antennas are basically assumed as the intensity receiving antennas in the aforementioned third and fourth embodiments, if all the receiving antennas are previously grouped, for example, only the grouped antennas are basically subjected to the intensity receiving antennas. Further, not all the receiving antennas but near receiving antennas predetermined for the video receiving antenna may be targeted. For example, when all the receiving antennas are denoted with serial numbers corresponding to the moving path of the capsule endoscope 3, the receiving antennas near the video receiving antenna, for example, having the previous and next two serial numbers may be targeted. When the receiving antennas are denoted with serial numbers, all the receiving antennas having larger numbers than that of the current video receiving antenna are subjected to the intensity receiving antennas.

Figure 14:
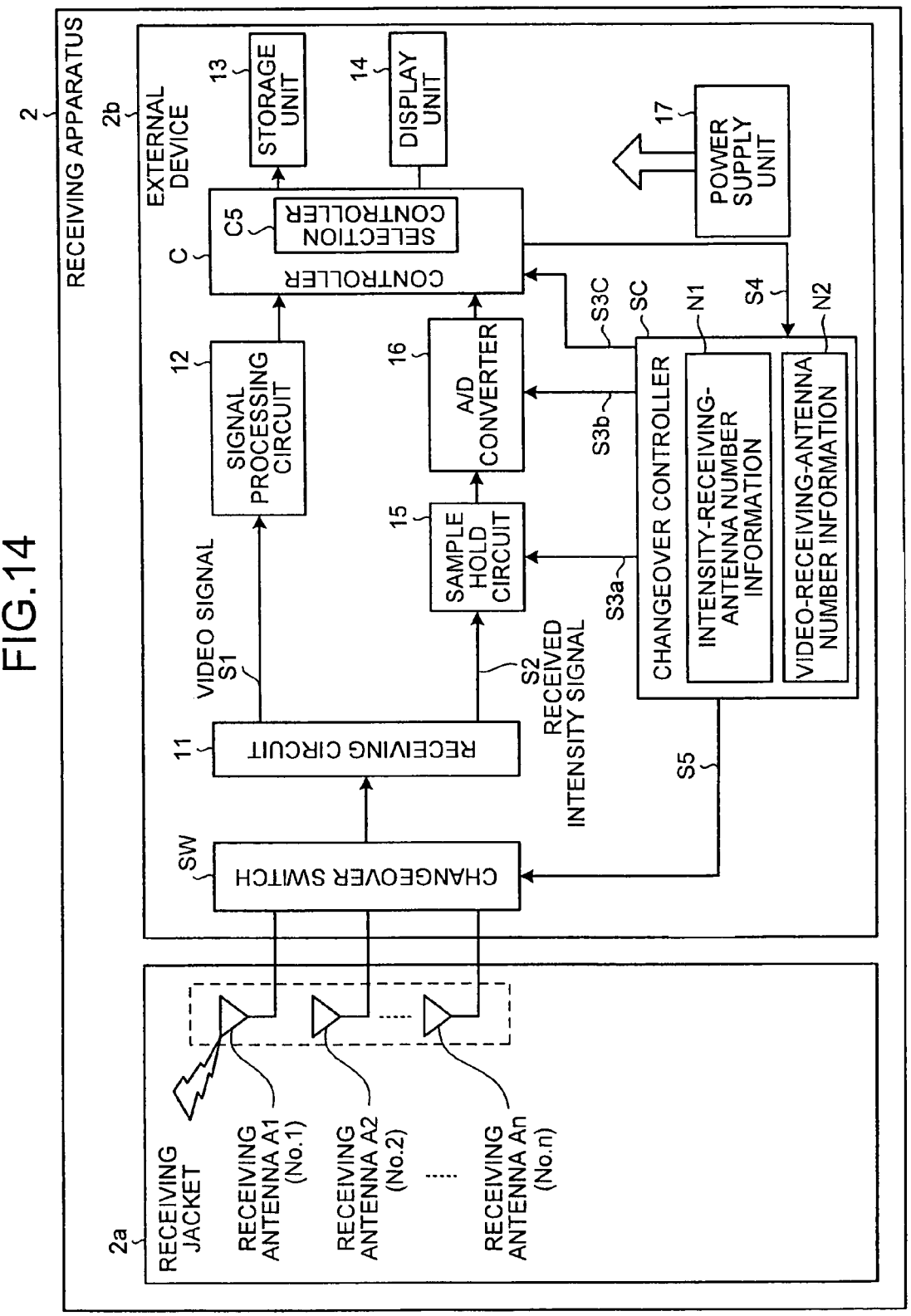
FIG. 14 is a block diagram showing a structure of a receiving apparatus according to a fifth embodiment of the present invention.

A fifth embodiment according to the present invention will now be described. The fifth embodiment is constituted so that the intensity receiving period is provided within the synchronization period and the synchronization signal is used to perform the receiving field intensity measurement during the intensity receiving period. FIG. 14 is a block diagram showing a structure of a receiving apparatus according to the fifth embodiment of the present invention. As shown in FIG. 14, this receiving apparatus is provided with a selection controller C5 instead of the selection controller C1. Other configurations are identical to those in the first embodiment and like numerals are denoted to like configurations.

Here, the intensity receiving period and video receiving period described above with reference to FIG. 15 and FIG. 16, that is, the frame structure of a radio signal will be described and an outline of a processing of selecting and changing over the receiving antennas A1 to An will be described. A radio signal transmitted from the capsule endoscope 3 is transmitted in unit of frame, and in this frame, the video signal period is conventionally provided after the intensity receiving period TS1, the synchronization period TS is provided at the head of the video signal period, and the video period TM made of m lines is provided subsequent to the synchronization period TS. In the fifth embodiment, the intensity receiving period TS1 is shifted to the synchronization period TS side and the synchronization signal is used as a signal for the receiving field intensity measurement. The synchronization signal is a pulse signal having a duty ratio of 50%, for example. When the receiving circuit 11 is constituted to be separated into an RF module for performing RF signal processing and a demodulating circuit for performing baseband demodulation, the synchronization processing for the RF module is performed in the first half of the synchronization period TS, and then the synchronization processing for the demodulating circuit is performed in the second half of the synchronization period TS.

Figure 15:
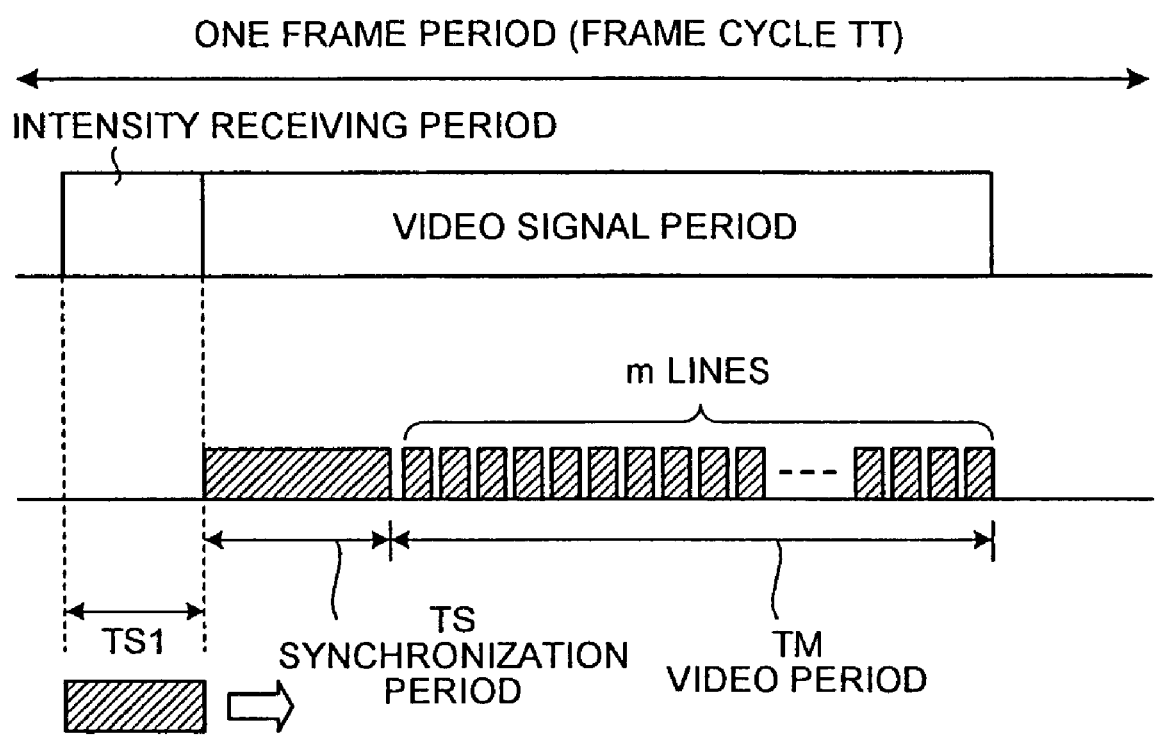
FIG. 15 is a diagram for explaining a frame format.

Each frame is transmitted as shown in FIG. 15 and a no-signal state may be between frames or each frame may be continuously transmitted. A frame cycle TT for frame transmission is short in an imaging area of interest or in an area where the capsule endoscope 3 fast moves in consideration of effective utilization of the battery of the capsule endoscope 3, and the length of the frame cycle TT is flexibly adjusted.

Figure 16:
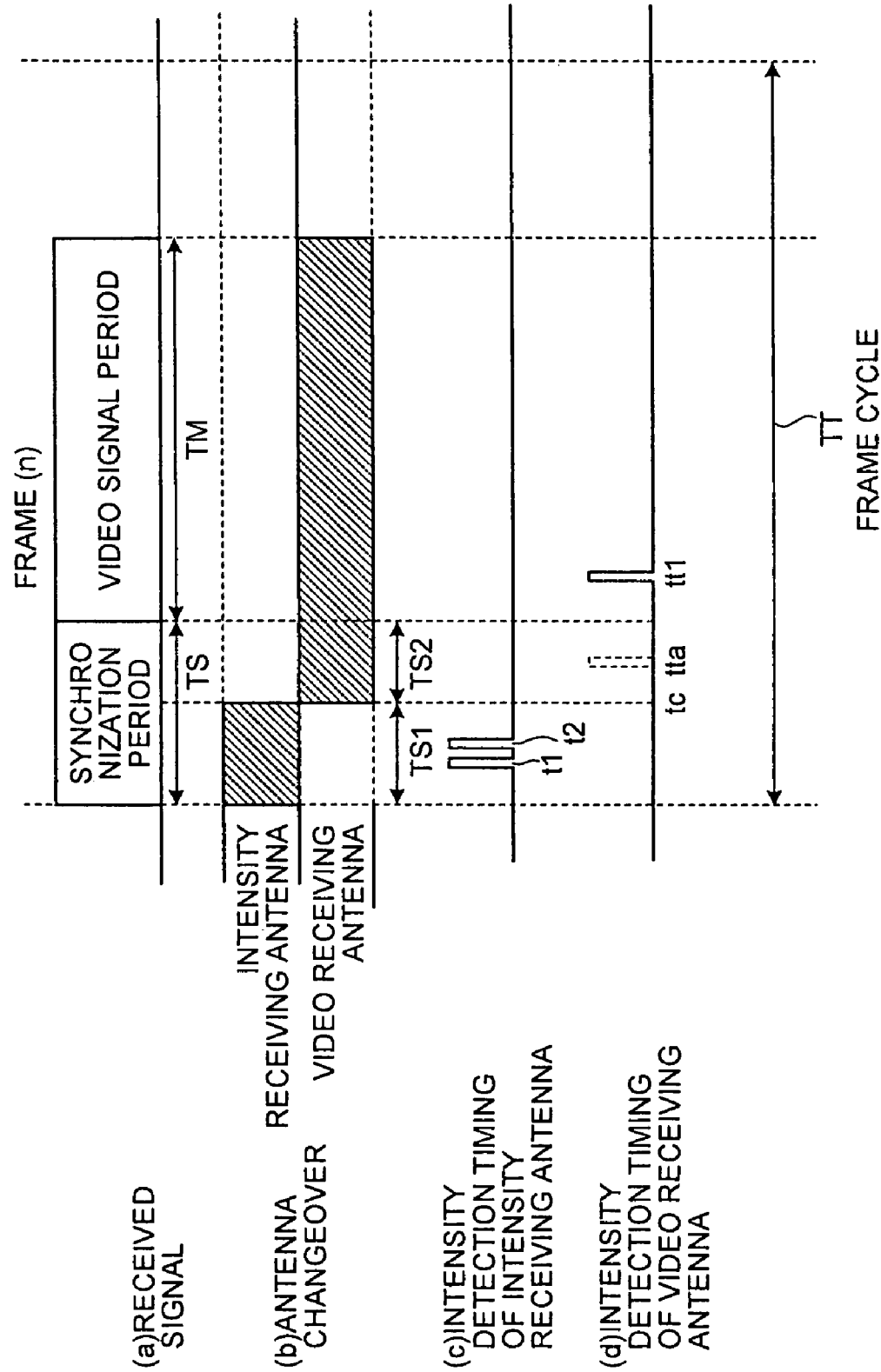
FIG. 16 is a timing chart for explaining an antenna changeover processing by the receiving apparatus shown in FIG. 14.

As shown in FIG. 16, the synchronization period TS in the n-th frame (n) has the intensity receiving period TS1 for selecting a receiving antenna having the largest receiving field intensity by using the synchronization signal and the synchronization period TS2 for the video signal, and antenna changeover is performed between the intensity receiving period TS1 and the synchronization period TS2. In FIG. 16, the synchronization signal is used in the intensity receiving period TS1 to change over two receiving antennas, and the receiving field intensity of each receiving antenna is sample-held and received at timings t1, t2 corresponding to the changed state, respectively. Thereafter, the receiving antenna for receiving the video signal is changed at timing tc within the synchronization period TS. The receiving circuit 11 performs the synchronization processing subsequent to the synchronization period corresponding to the intensity receiving period TS1 in the changed synchronization period TS2. Thereafter, the video signal made of m lines is received in the video period TM. The receiving field intensity of the video receiving antenna is measured at, for example, timing tt1 in the synchronization period TS2 and video period TM. The sample hold pulses at timings t1, t2, tt1 and tta are generated by the pulse generator 15a.

The selection controller C5 is constituted to select a receiving antenna having the largest receiving field intensity from among the receiving field intensities received in the intensity receiving period TS1 as the receiving antenna for the video signal period, but is not limited thereto and may be constituted to select a receiving antenna having the largest receiving field intensity, including the receiving field intensity of the video receiving antenna in addition to the receiving field intensities of the receiving antennas received in the synchronization period TS1, as the video receiving antenna.

The fifth embodiment is constituted so that the intensity receiving period TS1 is contained in the synchronization period TS, but is not limited thereto and may be constituted so that part of the intensity receiving period TS1 is overlapped on the synchronization period TS.

Since the fifth embodiment is constituted so that the intensity receiving period TS1 is provided in the synchronization period TS and the synchronization signal is used to perform the receiving field intensity measurement in the intensity receiving period TS1, the intensity receiving period does not require to be newly provided, thereby reducing the transmission power of the capsule endoscope 3 to be consumed per frame.

A sixth embodiment according to the present invention will now be described. A wireless in-subject information acquiring system shown in the sixth embodiment corresponds to the transmitting/receiving system and uses a capsule endoscope as one example of the transmitting apparatus (in-subject introducing apparatus).

Figure 17:
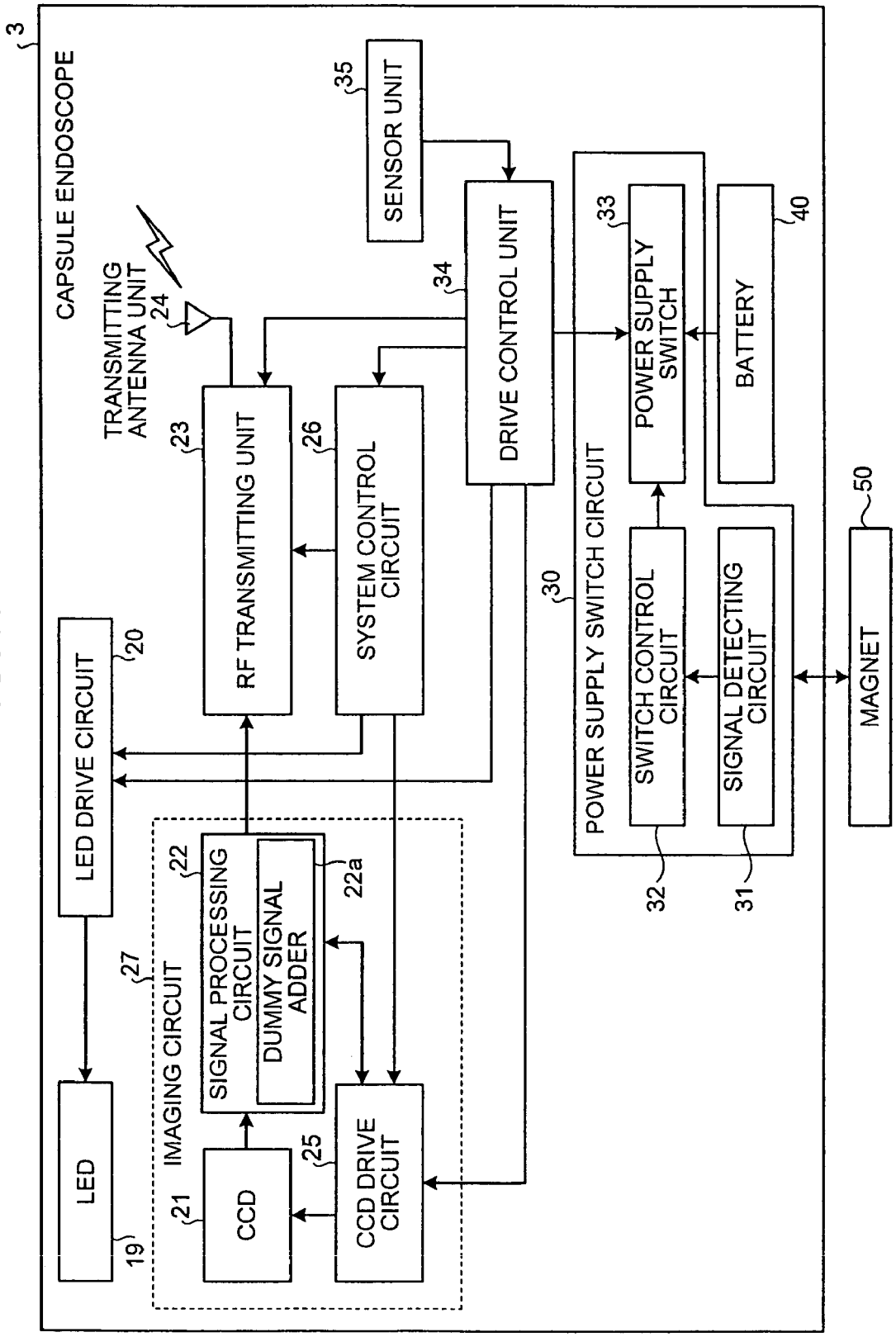
FIG. 17 is a block diagram showing a structure of a capsule endoscope according to a sixth embodiment of the present invention.

FIG. 17 is a block diagram schematically showing a structure of the capsule endoscope 3 according to the sixth embodiment of the present invention. As shown in FIG. 17, the capsule endoscope 3 comprises a TED 19 for radiating an imaging area when imaging the inside of the subject 1, a LED drive circuit 20 for controlling a drive state of the LED 19, a CCD 21 as imaging means for imaging an area radiated by the LED 19, and a signal processing circuit 22 for processing an image signal output from the CCD 21 into imaging information in a desired form. The capsule endoscope 3 further comprises a CCD drive circuit 25 for controlling a drive state of the CCD 21, an RF transmitting unit 23 for modulating image data imaged by the CCD 21 and processed by the signal processing circuit 22 to generate an RF signal, a transmitting antenna unit 24 for transmitting an RF signal output from the RF transmitting unit 23, and a system control circuit 26 for controlling operations of the LED drive circuit 20, the CCD drive circuit 25 and the RF transmitting unit 23. The CCD 21, the signal processing circuit 22 and the CCD drive circuit 25 are collectively called an imaging circuit 27.

The capsule endoscope 3 comprises the above mechanism to acquire image information of an inspected site radiated by the LED 19 through the CCD 21 while it is being introduced into the subject 1. The acquired image information is signal-processed into a video signal by the signal processing circuit 22 and converted into an RF signal in the RF transmitting unit 23, and then is transmitted to the outside via the transmitting antenna unit 24.

The signal processing circuit 22 comprises a dummy signal adder 22a, and the dummy signal adder 22a adds a dummy pulse for receiving intensity measurement used when synchronizing with the horizontal synchronization signal and the vertical synchronization signal of the video signal and detecting the receiving field intensity of each receiving antenna from a radio signal received by each receiving antenna described later within the vertical blanking period. For example, a counter is provided which is synchronized with the horizontal synchronization signal and the vertical synchronization signal, and a dummy pulse is generated by using a count value of the counter as a reference to be embedded in the vertical blanking period. The position or frequency of the dummy pulse is arbitrary if it is in the vertical blanking period.

The capsule endoscope 3 comprises a sensor unit 35 for detecting a signal of predetermined magnetism, light, radio wave or the like, and a drive control unit 34 for controlling the drive of the system control circuit 26 for entirely controlling the processings of the LED drive circuit, the CCD drive circuit 25, the RF transmitting unit 23 and the respective units. The sensor unit 35 is realized by, for example, a pH sensor, and detects whether the capsule endoscope 3 has reached a predetermined position in the subject so that the drive control unit 34 controls the driving of each unit based on the result. Thus, the power consumption can be restricted.

The drive control unit 34 is supplied with power for a battery 40 as an energy supply source via a power supply switch 33 in a power supply switch circuit 30. The battery 40 is realized by a button battery made of silver oxide, for example. The power supply switch 33 is a so-called main power supply switch of the capsule endoscope 3. The power supply switch circuit 30 further has a signal detecting circuit 31 and a switch control circuit 32. The signal detecting circuit 31 as external signal detecting means for detecting a signal from the outside of the capsule endoscope 3 is realized by a reed switch and is turned ON/OFF through proximity/separation of a magnet 50 with respect to the reed switch. In other words, the switch control circuit 32 which ON/OFF operates depending on whether a magnetic force acts on the reed switch controls to cause ON/OFF of the power supply switch 33 to perform toggle operation based on a control signal, that is, an ON/OFF signal from the signal detecting circuit 31. The ON/OFF of the power supply switch 33 by the magnet 50 is performed before being introduced into the subject to perform operation check of the capsule endoscope 3.

Figure 18:
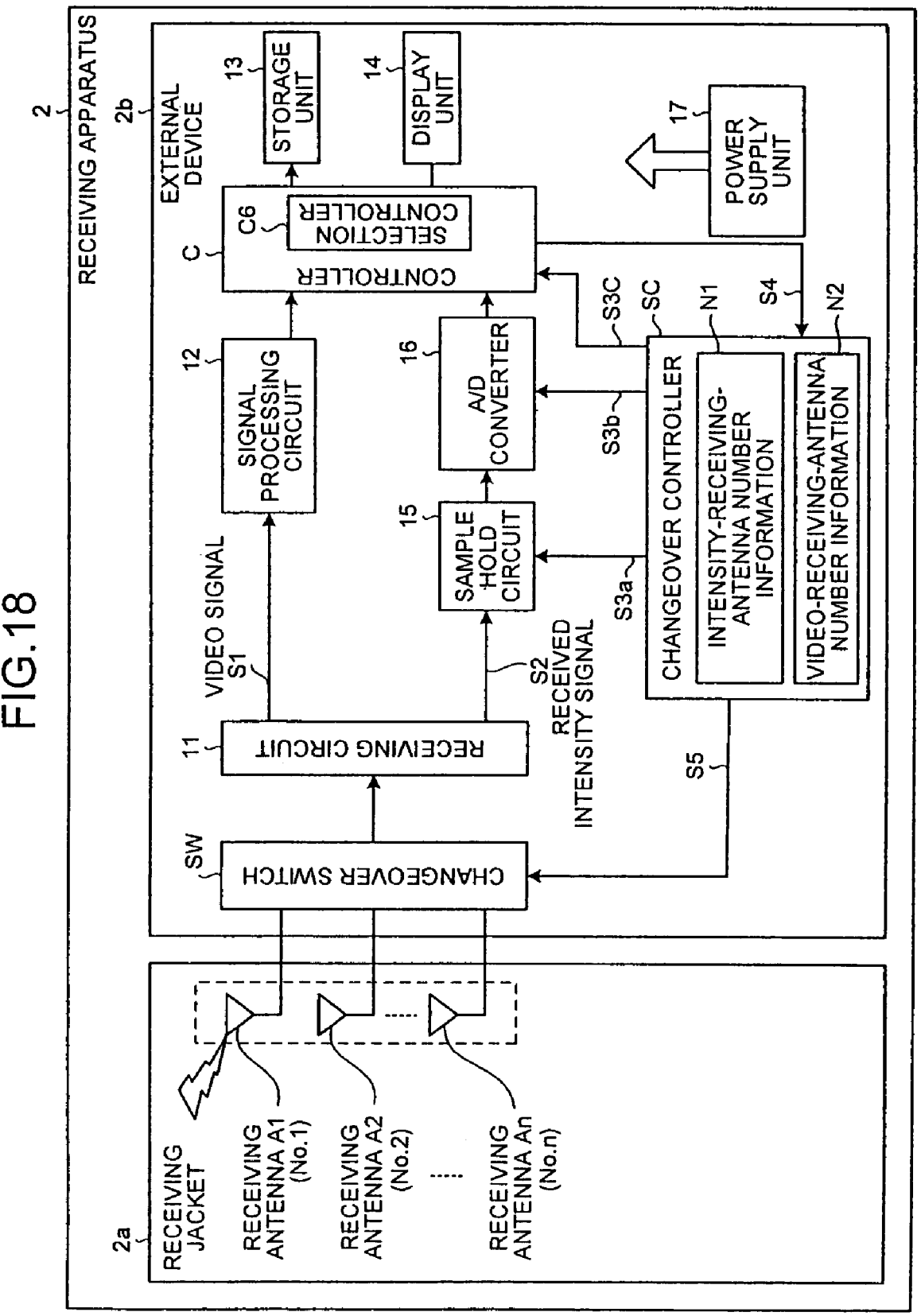
FIG. 18 is a block diagram showing a structure of a receiving apparatus according to the sixth embodiment of the present invention.

FIG. 18 is a block diagram showing a structure of a receiving apparatus according to the sixth embodiment of the present invention. As shown in FIG. 18, the receiving apparatus is provided with a selection controller C6 instead of the selection controller C1. Other configurations are identical to those in the first embodiment and like numerals are denoted to like configurations.

Figure 19:
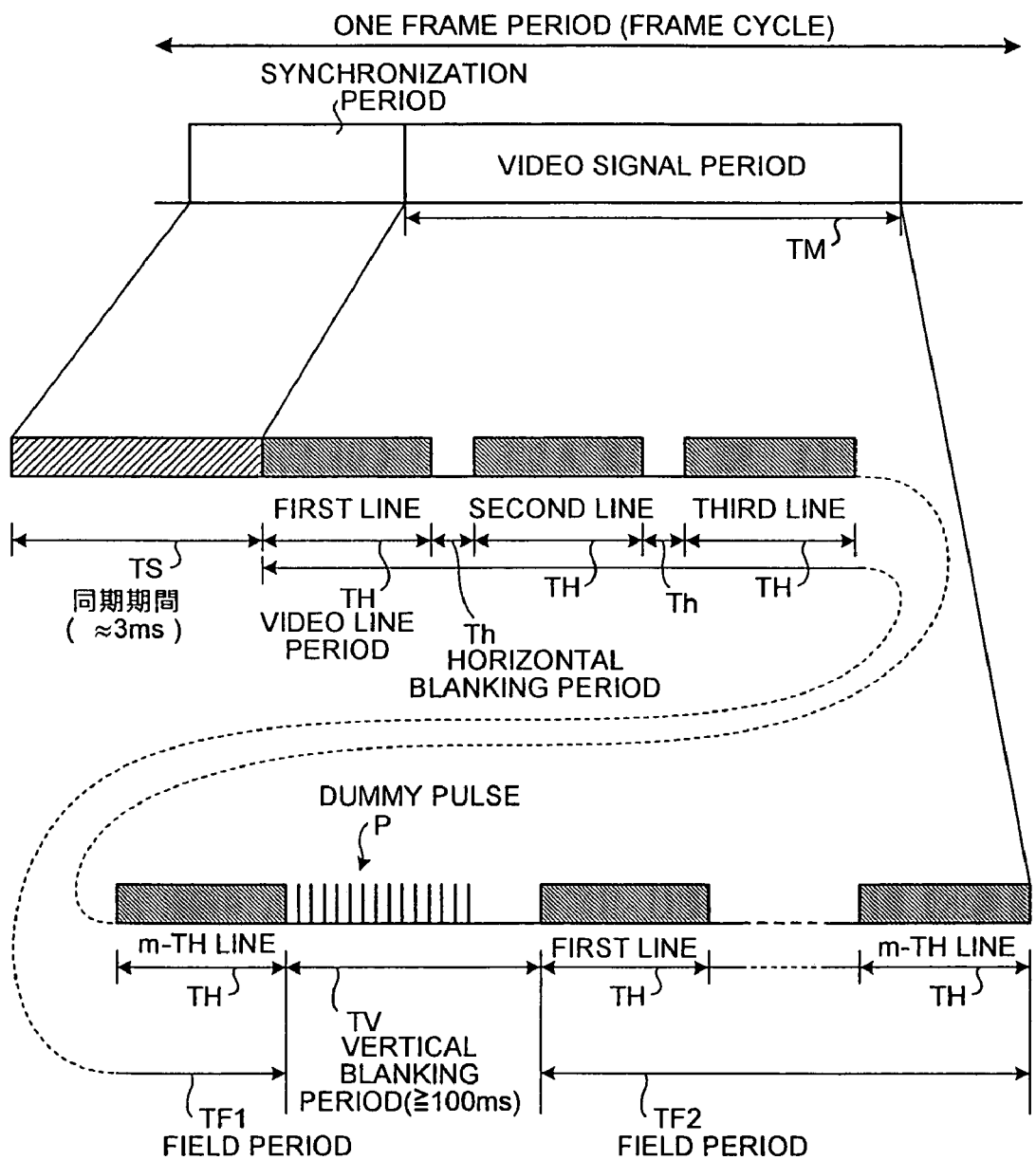
FIG. 19 is a diagram showing a frame format of a radio signal transmitted from the capsule endoscope shown in FIG. 17.

Here, the synchronization period and video receiving period described above with reference to FIG. 19 and FIG. 20, that is, the frame structure of a radio signal will be described, and a processing of selecting and changing over the receiving antennas A1 to An will be described. A radio signal transmitted from the capsule endoscope 3 is transmitted in unit of frame, and the frame is constituted, as shown in FIG. 19, of the synchronization period TS as the additional part including information for synchronization and the video signal period TM as the information body part including information body. The synchronization period TS is a period corresponding to the preamble signal period for receiving adjustment. Further, the video signal period TM is a period for receiving a video signal, and the video signal has a field period TF1 in which odd-numbered field signals are transmitted, a vertical blanking period TV and a field TF2 in which even-numbered field signals are transmitted. A dummy pulse P added by the dummy signal adder 22a is inserted into the vertical blanking period TV as described above. A control signal necessary for receiving the video signal may be included in the video signal period TM in addition to the horizontal video signal itself.

The synchronization period and the video receiving period may be provided as independent periods or may be provided as overlapped periods.

Figure 20:
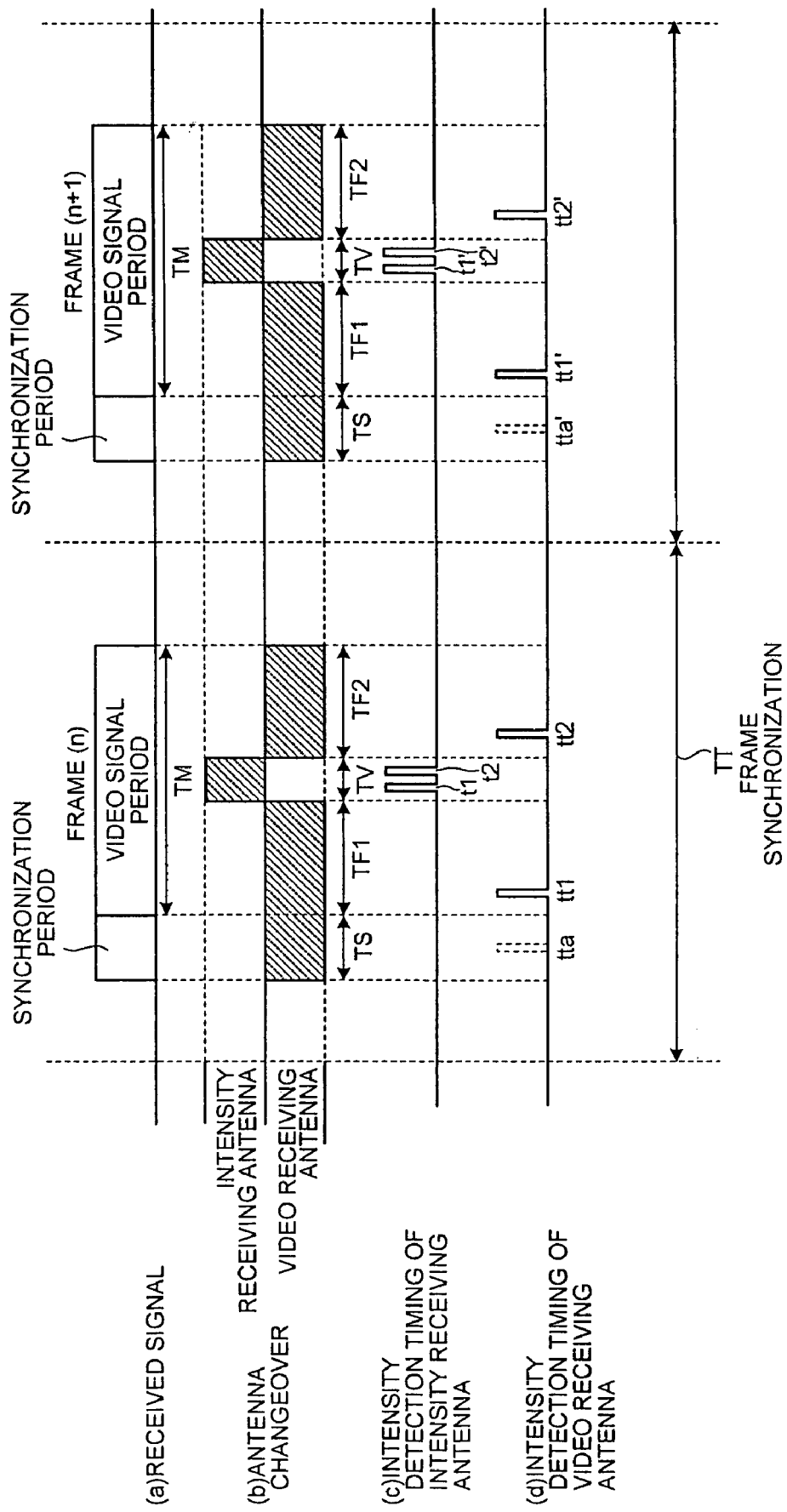
FIG. 20 is a time chart showing a processing for receiving field intensity measurement and antenna changeover by the receiving apparatus shown in FIG. 18.

Each frame is transmitted as shown in FIG. 20 and a no-signal state may be between frames or each frame may be continuously transmitted. A frame cycle TT for frame transmission is short in an imaging area of interest or in an area where the capsule endoscope 3 fast moves in consideration of effective utilization of the battery of the capsule endoscope 3, and the length of the frame cycle TT is flexibly adjusted.

As shown in FIG. 20, the receiving antenna is changed over between the field periods TF1, TF2 and the vertical blanking period TV in the n-th frame (n). The video receiving antenna stands for a receiving antenna for receiving in the synchronization period TS and each field period TF1, TF2. The intensity receiving antenna stands for a receiving antenna for receiving in the vertical blanking period TV. The selection controller C1 measures the receiving field intensity in the period for changing to the intensity receiving antenna, selects and changes a receiving antenna having the largest receiving field intensity including the receiving field intensity of the current video receiving antenna as the receiving antenna in the period for changing to the next video receiving antenna, and selects the intensity receiving antenna except for at least the immediately previous video receiving antenna in the period for changing to the next intensity receiving antenna. A receiving antenna having the largest receiving field intensity at the point is selected as the video receiving antenna through the above repetition.

A timing at which the receiving antenna having the largest receiving field intensity is selected may be selected after a predetermined number of times of the receiving field intensity measurement, and the video receiving antenna selected at the previous time may be selected during the measurement. Since the moving path of the capsule endoscope 3 is previously known, the odd-numbered field in the frame to be first transmitted previously selects the video receiving antenna and the video receiving antenna of the odd-numbered field in the second and subsequent frames may set the receiving antenna selected in the vertical blanking period TV in the first frame.

In FIG. 20, the receiving field intensity measurement is performed twice at timings t1 and t2 in the vertical blanking period TV, but is not limited thereto and may be performed only one time or more than three times. When performing the receiving field intensity measurement several times, it is preferable to perform the receiving field intensity measurement for different receiving antennas. The field intensity of the video receiving antenna is measured at timing tt1 in the field period TF1, but the receiving field intensity may be measured at timing tta in the synchronization period TS. The timings t1, t2, tt1 and tt2 are pulses generated by the pulse generator 15*a*. Here, the receiving field intensity measurement is performed in the horizontal blanking period TV added with a dummy pulse P, but even when the dummy pulse is added to the entire vertical blanking period TV, the receiving field intensity measurement may not be performed for the entire horizontal blanking period TV.

The antenna changeover between the field period TF1, TF2 and the vertical blanking period TV is possible with high accuracy because it can use the synchronization of the vertical blanking period.

The synchronization period TS is about 3 ms, and a period as long as the synchronization period TS may be added before the synchronization period as a period for the receiving field measurement to measure the receiving field intensity. But, since the vertical blanking period TV is a period of 100 ms or more, the receiving field intensity for many receiving antennas can be measured in the period. Naturally, the synchronization period for the receiving field measurement may be a format to be added before the synchronization period TS.

Since the sixth embodiment is constituted so that the dummy pulse P for the receiving field intensity measurement is added to the vertical blanking period TV to perform the receiving field intensity measurement for selecting the video receiving antenna in the long vertical blanking period TV, the optimum video receiving antenna having the largest receiving field intensity can be selected with high accuracy. Further, the synchronization period can be reduced and consequently the transmission time in the frame is reduced, thereby achieving power saving of the capsule endoscope 3.

Figure 21:
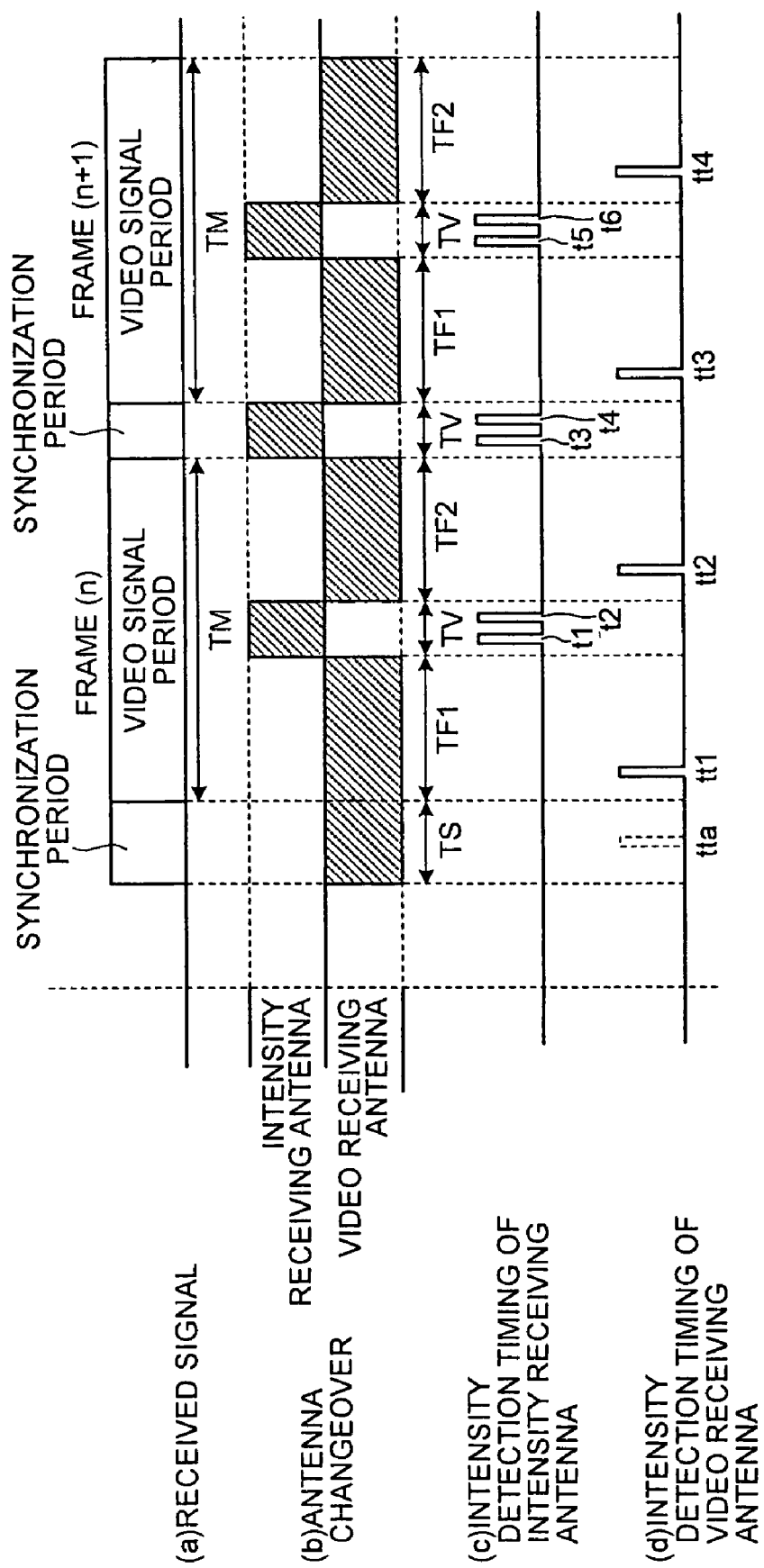
FIG. 21 is a time chart showing a variant of the processing for receiving field intensity measurement and antenna changeover by the receiving apparatus shown in FIG. 18.

In the sixth embodiment, description is made as each frame being transmitted without synchronization between frames, but in the case of 2-frame transmission, it is preferable that the vertical blanking period is provided between frames and the receiving field intensity measurement for selecting the optimum video receiving antenna is performed even in the vertical blanking period similarly as in the vertical blanking period between the fields TF1 and TF2 (refer to FIG. 21). Further, although the imaging in an interlace manner has been described in the aforementioned sixth embodiment, in the case of the interlace manner, if the frames are continuously transmitted, the vertical blanking period TV occurs, thereby applying the present embodiment.

A seventh embodiment according to the present invention will now be described. The seventh embodiment is constituted so that a dummy pulse for the receiving field intensity measurement is added in the horizontal blanking period in the video signal period to perform the receiving field intensity measurement for selecting the video receiving antenna in the long horizontal blanking period.

Figure 22:
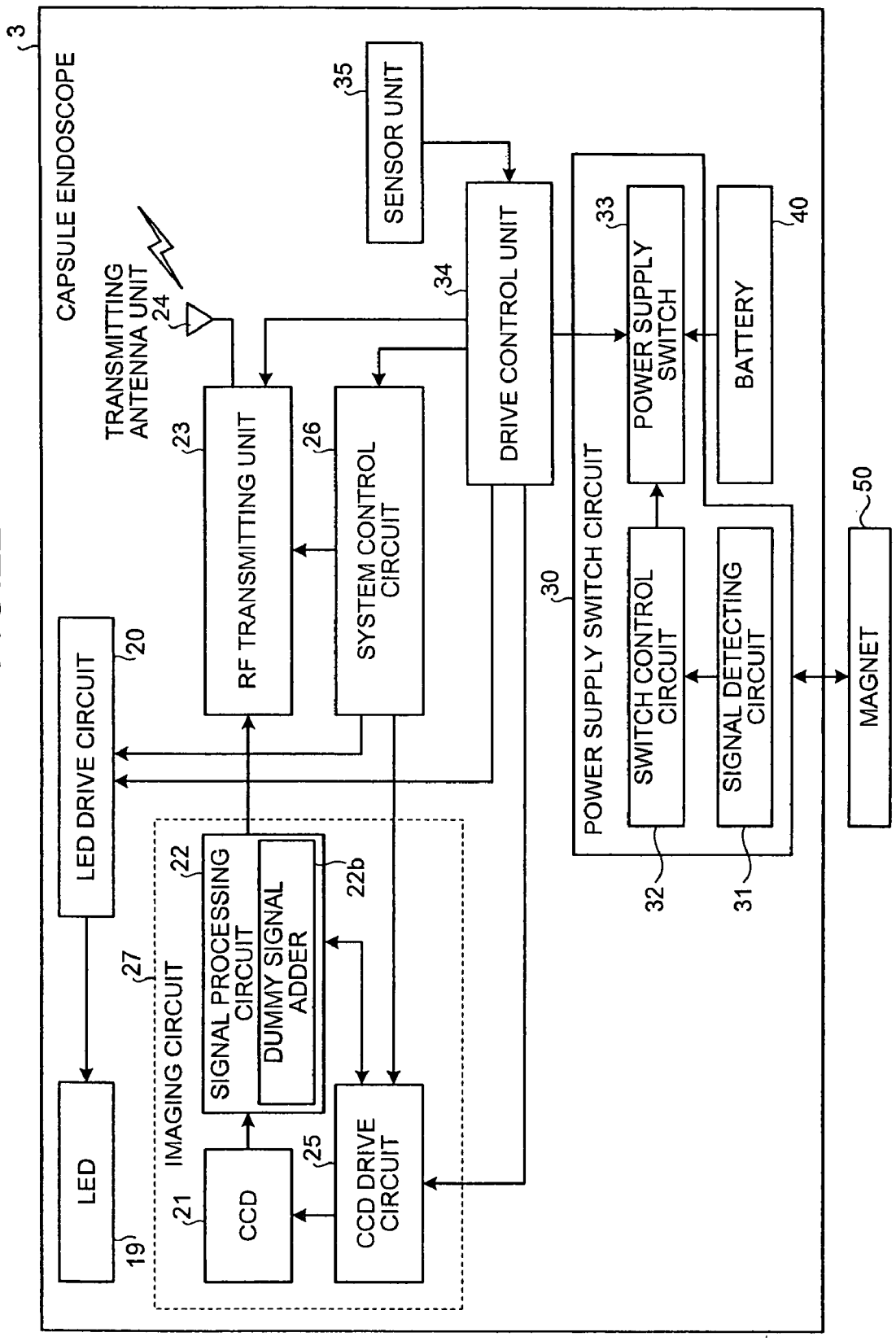
FIG. 22 is a block diagram showing a structure of a capsule endoscope 3 according to a seventh embodiment of the present invention.
Figure 23:
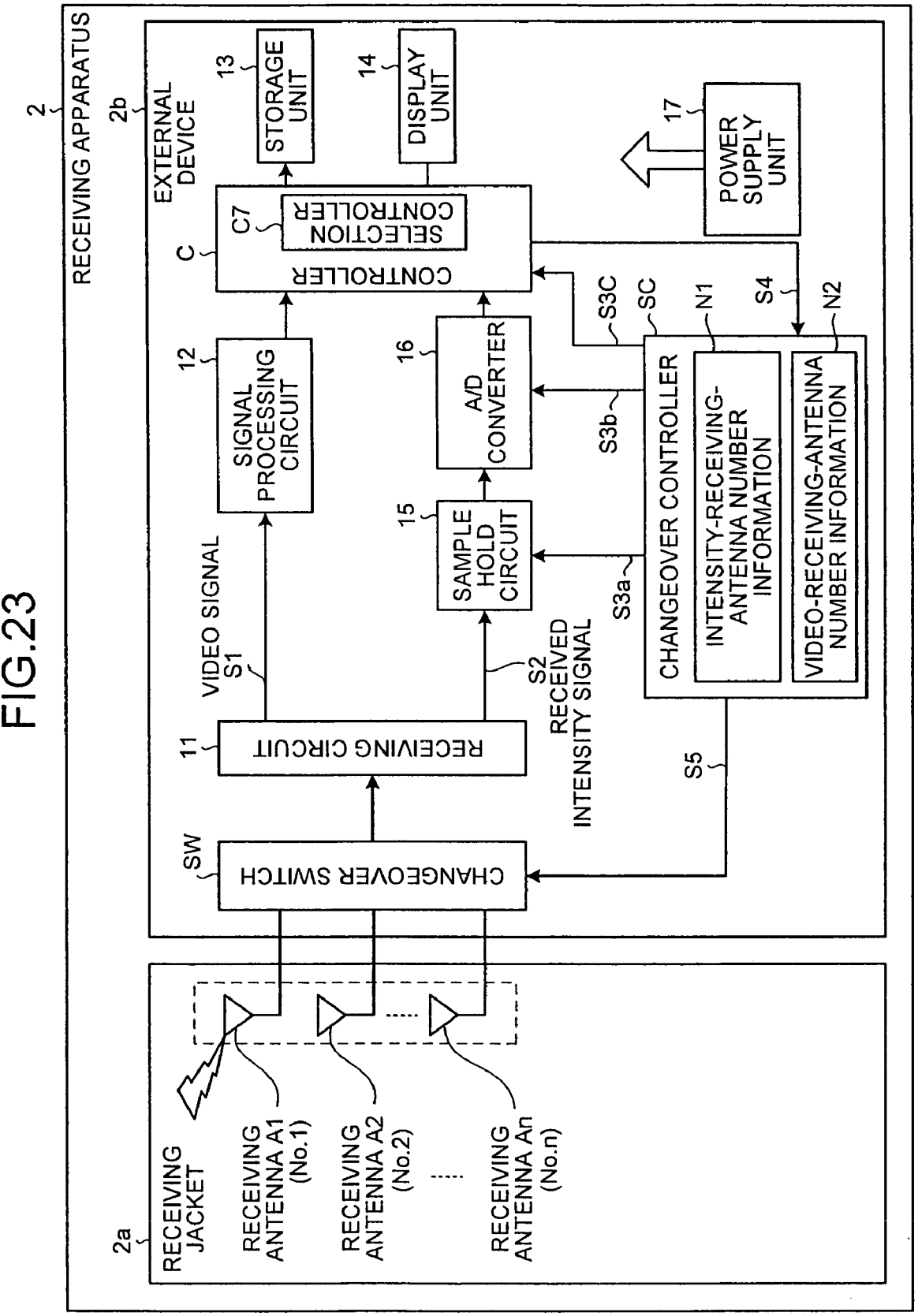
FIG. 23 is a block diagram showing a structure of a receiving apparatus according to the seventh embodiment of the present invention.

FIG. 22 is a block diagram schematically showing a structure of a capsule endoscope according to the seventh embodiment of the present invention. As shown in FIG. 22, the capsule endoscope 3 is provided with a dummy signal adder 22*b* instead of the dummy signal adder 22*a* shown in FIG. 17*a*. Further, FIG. 23 is a block diagram showing a structure of a receiving apparatus according to the seventh embodiment of the present invention. As shown in FIG. 23, the receiving apparatus is provided with a selection controller C7 instead of the selection controller C1. Other configurations are identical to those in the sixth embodiment and like numerals are denoted to like configurations.

As shown in FIG. 22, the signal processing circuit 22 comprises the dummy signal adder 22*b*, and the dummy signal adder 22*b* adds a dummy pulse for the receiving intensity measurement used when synchronizing with the horizontal synchronization signal and vertical synchronization signal of the video signal and detecting the receiving field intensity of each antenna from the radio signal received by each receiving antenna described later during the horizontal blanking period. For example, a counter is provided which synchronizes with the horizontal synchronization signal and the vertical synchronization signal, and a dummy pulse is generated by using a count value of the counter as a reference to be embedded in the horizontal blanking period. The position or frequency of the dummy pulse is arbitrary if it is in the horizontal blanking period. It is not necessary to add the dummy pulse to all the horizontal blanking periods, and the dummy pulse may be added to only the required horizontal blanking periods.

Figure 24:
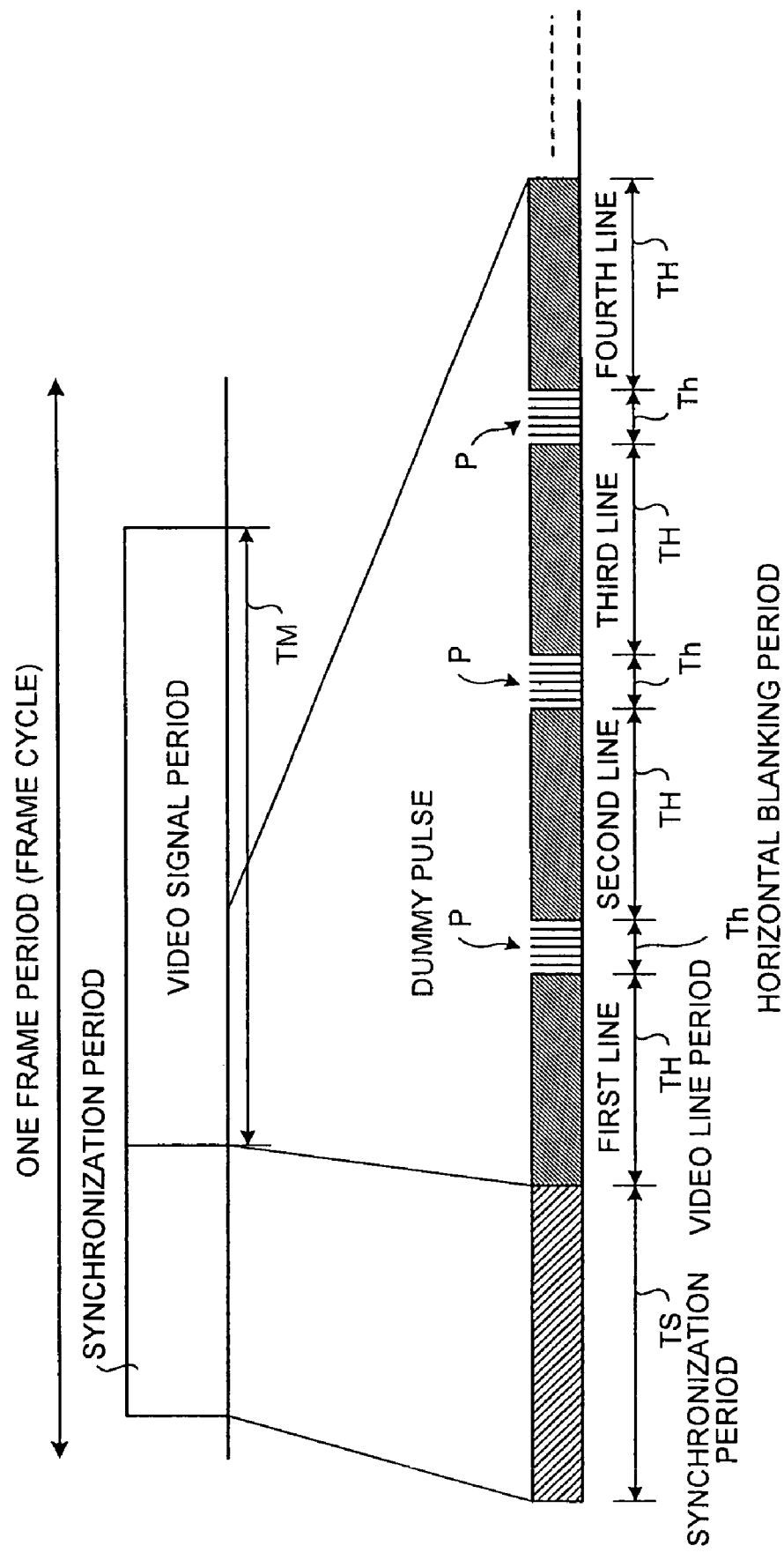
FIG. 24 is a diagram showing a frame format of a radio signal transmitted from the capsule endoscope shown in FIG. 22.

The synchronization period and video receiving period described above with reference to FIG. 24 and FIG. 25, that is, the frame structure of a radio signal will be described and a processing of selecting and changing over the receiving antennas A1 to An will be described. A radio signal transmitted from the capsule endoscope 3 is transmitted in unit of frame, and, as shown in FIG. 24, the frame is constituted of the synchronization period TS as the additional part including information for synchronization and the video signal period TM as the information body part including information body. The synchronization period TS is a period corresponding to the preamble signal period for receiving adjustment. The video signal period TM is a period for receiving a video signal, and the video signal has a video line period TH in which a video line signal for each line is transmitted and a horizontal blanking period Th inserted between the video line periods TH. A dummy pulse P added by the dummy signal adder 22a is inserted into the horizontal blanking period Th as described above. The video signal period TM can contain a control signal necessary for receiving the video signal in addition to the horizontal video signal itself. The synchronization period and the video receiving period may be provided as independent periods or may be provided as overlapped periods.

Figure 25:
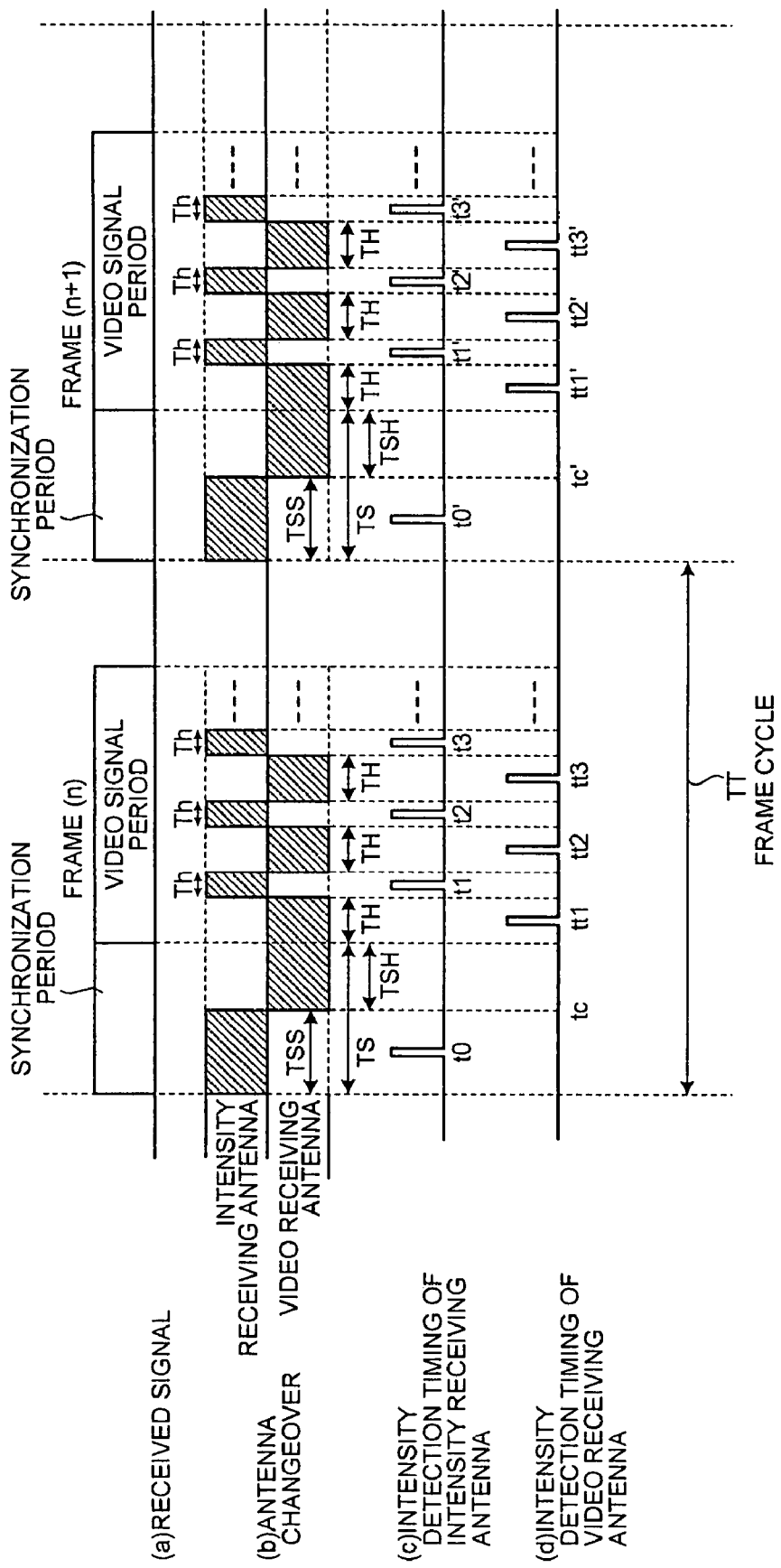
FIG. 25 is a time chart showing the processing for receiving field intensity measurement and antenna changeover by the receiving apparatus shown in FIG. 23.

Each frame is transmitted as shown in FIG. 25 and a no-signal state may be between frames or each frame may be continuously transmitted. A frame cycle TT for frame transmission is short in an imaging area of interest or in an area where the capsule endoscope 3 fast moves in consideration of effective utilization of the battery of the capsule endoscope 3, and the length of the frame cycle TT is flexibly adjusted.

As shown in FIG. 25, the receiving antenna is changed over at timing tc in the synchronization period TS in the n-th frame (n) and the receiving antenna is changed over between the video line period TH and the horizontal blanking period Th. The video receiving antenna stands for a receiving antenna for receiving in a period TSH after timing tc in the synchronization period TS and the video line period TH at the first line as well as each video line period TH after the second line. The intensity receiving antenna stands for a receiving antenna for receiving in a period TSS before timing tc in the synchronization period TS and each horizontal blanking period Th. The selection controller C1 measures the receiving field intensity in a period for changing to the intensity receiving antenna, selects and changes a receiving antenna having the largest receiving field intensity including the receiving field intensity of the current video receiving antenna as the receiving antenna in a period for changing to the next video receiving antenna, and selects the intensity receiving antenna except for at least the immediately previous video receiving antenna in a period for changing to the next intensity receiving antenna. A receiving antenna having the largest receiving field intensity at the point is selected as the video receiving antenna through the above repetition.

The timing at which the receiving antenna having the largest receiving field intensity is selected may be selected after a predetermined number of times of the receiving field intensity measurement, and the video receiving antenna selected at the previous time may be selected. For example, the video receiving antenna may be selected and determined in unit of frame. In this case, the video receiving antenna selected and determined in the frame (n) is used as the video receiving antenna in the next frame (n+1).

In FIG. 25, the receiving field intensity measurement is performed once in the period TSS before timing tc in the synchronization period TS and each horizontal blanking period Th, respectively, but is not limited thereto and the receiving field intensity measurement may be performed several times, and in this case, the receiving field intensity measurement for a plurality of different receiving antennas may be performed. The timings t0 to t2 and tt1 to tt3 are pulses generated by the pulse generator 15a. Here, although the receiving field intensity measurement is performed in the horizontal blanking period Th added with the dummy pulses P, even when the dummy pulses are added to all the horizontal blanking periods Th, the receiving field intensity measurement may not be performed for all the horizontal blanking periods Th.

The antenna changeover between the video line period TH and the horizontal blanking period Th is possible with high accuracy because it can use the synchronization of the horizontal blanking.

Since the seventh embodiment is constituted so that the dummy pulse P for the receiving field intensity measurement is added in the horizontal blanking period Th in the video signal period TM to perform the receiving field intensity measurement for selecting the video receiving antenna in the long horizontal blanking period Th, the optimum video receiving antenna having the largest receiving field intensity can be selected with high accuracy and fineness.

Figure 26:
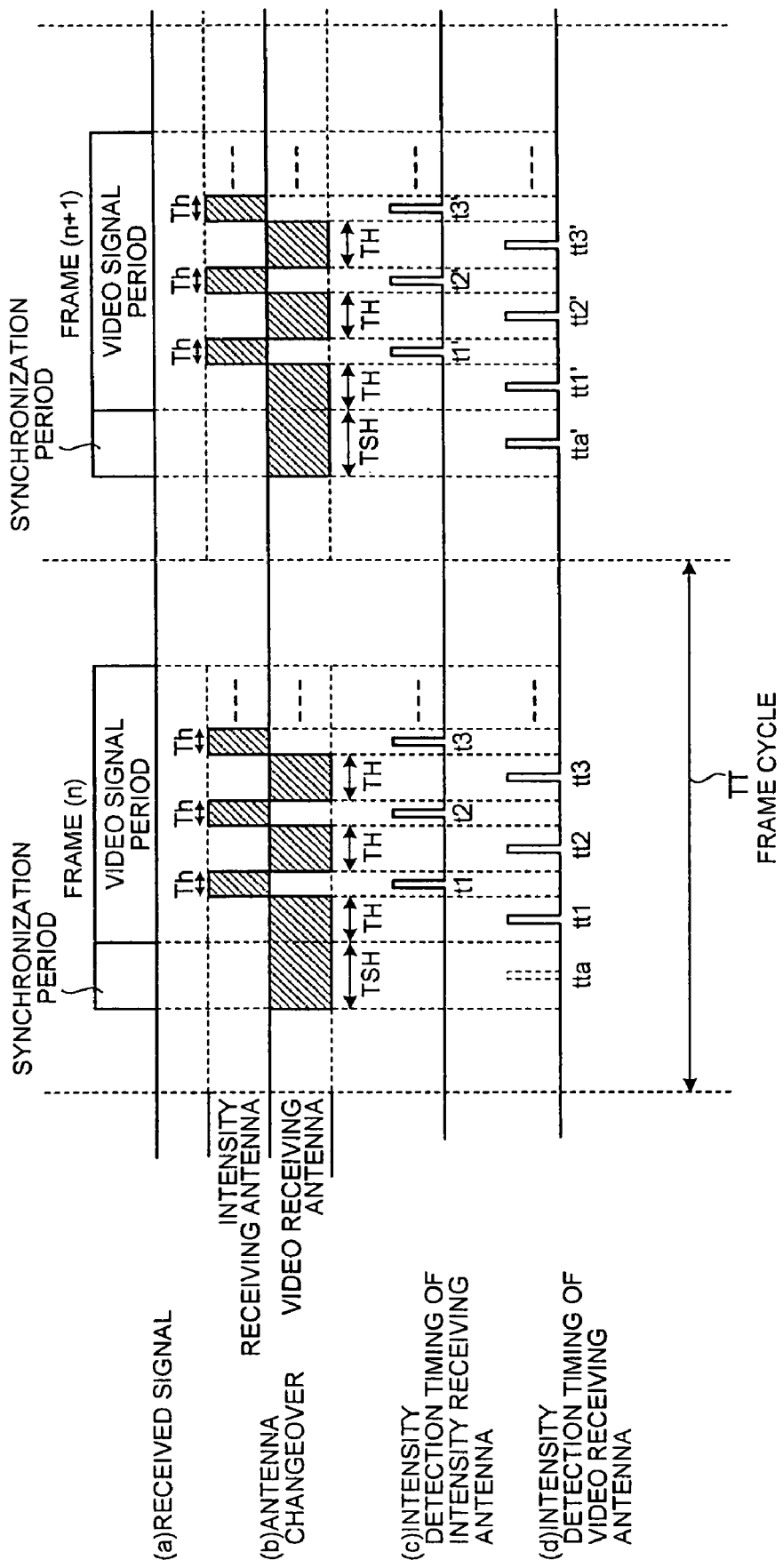
FIG. 26 is a time chart showing a variant of the processing for receiving field intensity measurement and antenna changeover by the receiving apparatus shown in FIG. 23.

In the aforementioned seventh embodiment, although the antenna changeover is performed at timing tc in the synchronization period TS, since the receiving field intensity measurement sufficient for selecting the optimum video receiving antenna can be performed only in the horizontal blanking period Th, it is preferable that the synchronization period TSS is deleted to assume the synchronization period TSH having only the period TSH necessary for the synchronization of the video signal receiving as shown in FIG. 26. In this case, the synchronization period can be reduced and consequently the transmission time in the frame is reduced, thereby achieving the power saving of the capsule endoscope 3.

An eighth embodiment according to the present invention will now be described. The eighth embodiment is constituted so that only the receiving antennas A1 to An connected to the changeover switches are set as the intensity receiving antennas.

Figure 27:
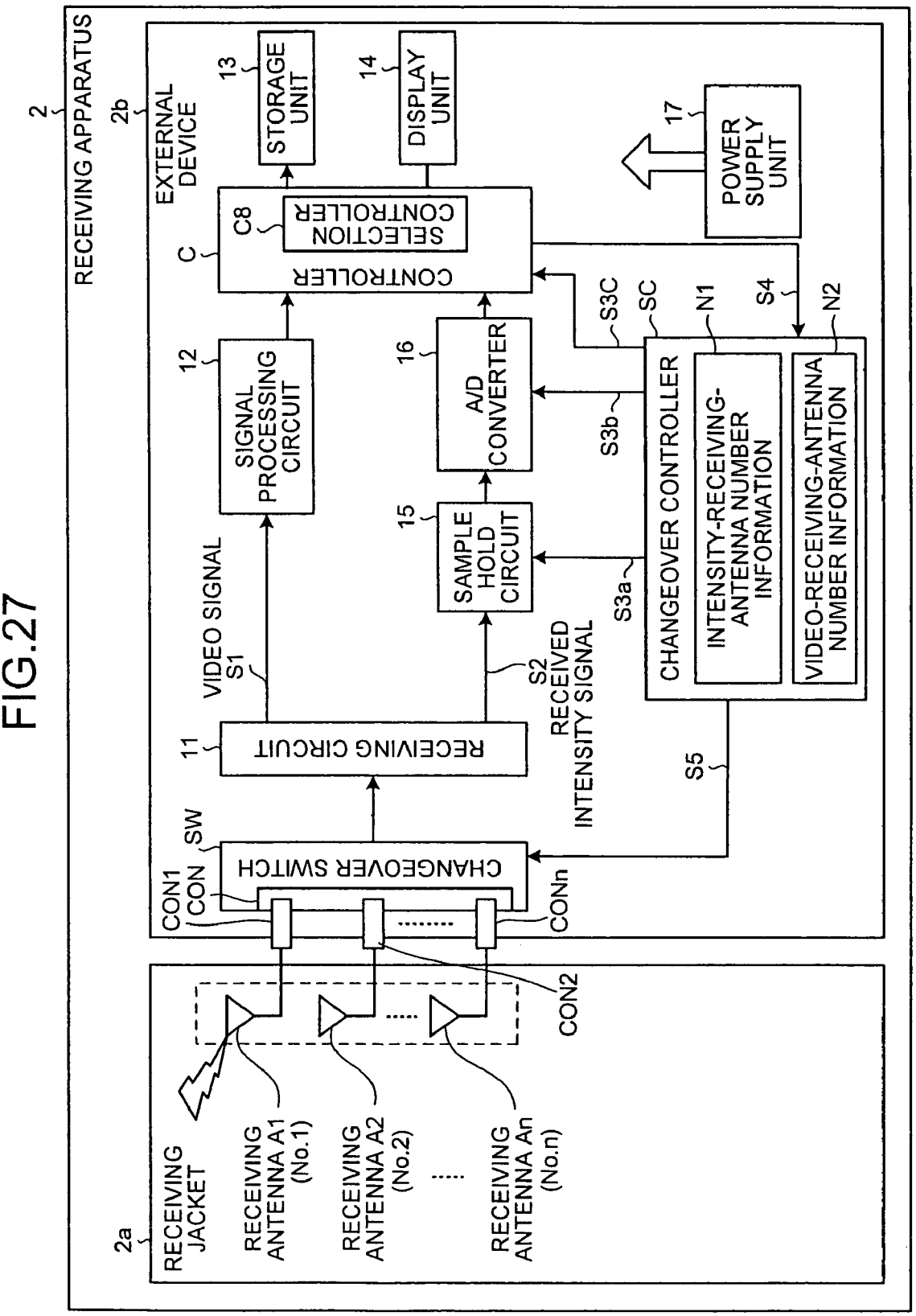
FIG. 27 is a block diagram showing a structure of a receiving apparatus according to an eighth embodiment of the present invention.

FIG. 27 is a block diagram showing a structure of a receiving apparatus according to the eighth embodiment of the present invention. As shown in FIG. 27, the receiving apparatus is provided with a changeover switch SW2 having a connecting unit COM with connectors CON1 to CONn instead of the changeover switch SW and a selection controller C8 instead of the selection controller C1. Other configurations are identical to those in the first embodiment and like numerals are denoted to like configurations.

The changeover switch SW2 of the external device 2b selectively changes any one of the receiving antennas A1 to An based on the changeover instruction from the changeover controller SC, and outputs a radio signal from the changed receiving antenna A1 to An to the receiving circuit 11. Here, the changeover switch SW2 has the connecting unit CON as antenna changeover means for connecting each receiving antenna A1 to An in correspondence to the arrangement position of the receiving antenna A1 to An. On the other hand, each receiving antenna A1 to An has a connector CON1 to CONn connected to the connecting unit CON.

Figure 28:
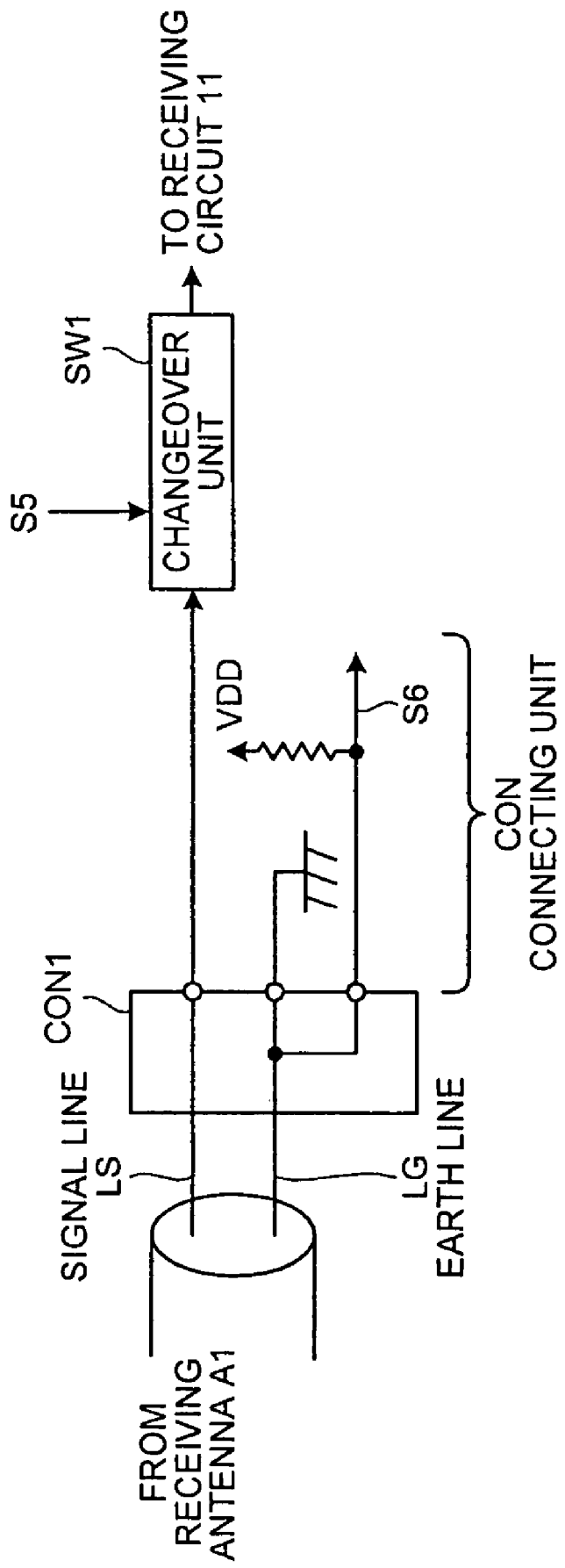
FIG. 28 is a diagram showing a structure of a connecting unit within a changeover switch.

The connecting unit CON has a detecting function of detecting a connection state of each connector CON1 to CONn. For example, the connecting unit CON has a detecting circuit as shown in FIG. 28 for the connector CON1 and has a similar detecting circuit also for other connector CON2 to CONn. In FIG. 28, the connector CON1 connects a signal line LS and an earth line LG from the receiving antenna A1 to the connecting unit CON and branches the earth line LG for output. The connecting unit CON outputs the signal line LS to the changeover unit SW1 as it is, which is changed over based on the signal S5 instructing the changeover and is output to the receiving circuit 11. On the other hand, one end of the earth line LG is grounded as it is and the other end of the earth line LG is connected to a constant voltage source VDD. When the connector CON1 is connected to the connecting unit CON, a voltage signal from the constant voltage source VDD flows to one end of the earth line LG so that a signal S6 is not output to the selection controller C1 of the external controller C, and when the connector CON1 is not connected to the connecting unit CON, the voltage signal from the constant voltage source VDD is output to the selection controller C1 as the signal S6 as it is. Therefore, the selection controller C1 detects the presence of the signal S6 as the voltage signal to determine whether the connector CON1, that is, the receiving antenna A1 is connected. A similar detecting circuit is provided in correspondence to each connector CON2 to CONn so that the selection controller C1 can senses the connection state of each receiving antenna A1 to An.

In FIG. 27, the receiving circuit 11 amplifies a radio signal and outputs the demodulated video signal S1 to the signal processing circuit 12, and outputs the received intensity signal S2 indicating the receiving field intensity of the amplified radio signal to the sample hold circuit 15. The video data processed by the signal processing circuit 12 is stored in the storage unit 13 by the controller C, and is displayed and output by the display unit 14. The signal subjected to sample-hold by the sample hold circuit 15 is converted into a digital signal by the A/D converter 16 to be fetched in the controller C, and the selection controller C1 of the controller C selects a receiving antenna having the largest receiving field intensity from among the receiving field intensities received in the intensity receiving period described later as the receiving antenna for the video signal period, and sequentially selects the receiving antenna other than the selected receiving antenna as the receiving antenna for the intensity receiving period, and outputs it as the signal S4 which assumes the respective receiving antenna numbers as the video-receiving-antenna number information N2 and the intensity-receiving-antenna number information N1 to the changeover controller SC. Here, the selection controller C1 selects only the currently connected receiving antenna A1 to An based on the signal S6 as the receiving antenna to be changed over. Further, the controller C stores the receiving field intensity in the intensity receiving period and the receiving field intensity in the video receiving period in the storage unit 13 together with the video data in correspondence to the selected receiving antenna. The stored receiving field intensity of each receiving antenna is information for calculating the position of the capsule endoscope 3 in the body when the video data is received.

Here, the intensity receiving period and video receiving period described above with reference to FIG. 5 and FIG. 29, that is, the frame structure of a radio signal will be described and an outline of a processing of selecting and changing over the receiving antenna A1 to An will be described. A radio signal transmitted from the capsule endoscope 3 is transmitted in unit of frame, and as shown in FIG. 5, the frame is constituted of the intensity receiving period as the additional part including information for the receiving field intensity measurement and the video signal period as the information body part including information body. The intensity receiving period is a period corresponding to the preamble signal period for receiving adjustment. Further, the video signal period can contain a control signal necessary for receiving the video signal in addition to the video signal itself. The intensity receiving period and the video receiving period may be provided as independent periods or may be provided as overlapped periods.

Each frame is transmitted as shown in FIG. 29 and a no-signal state may be between frames or each frame may be continuously transmitted. A frame cycle TT for frame transmission is short in an imaging area of interest or in an area where the capsule endoscope 3 fast moves in consideration of effective utilization of the battery of the capsule endoscope 3, and the length of the frame cycle TT is flexibly adjusted.

As shown in FIG. 29, when the n-th frame (n) and the (n+1)-th frame (n+1) are sequentially transmitted, other receiving antenna (intensity receiving antenna) different from the receiving antenna (video receiving antenna) for receiving in the video signal period of the same frame (n) is changed over in the period ta corresponding to the intensity receiving period of the frame (n) and the video receiving antenna is changed over in the period tb including the video receiving period and the period to the start of the intensity receiving period of the next frame (n+1). Similarly, the intensity receiving antenna is changed over in the video signal period of the same frame (n+1) in a period ta' corresponding to the intensity receiving period of the frame (n+1), and the video receiving antenna is changed over in a period tb' including the video receiving period and the period to the start of the intensity receiving period of the next frame (n+2).

The intensity detection processing is performed by the sample hold circuit 15 and the A/D converter 16 at timing t1, t1' during the intensity receiving period of the frame (n) and the frame (n+1), and the result thereof is output to the selection controller C1. When fast changeover of the receiving antenna or fast receiving field intensity measurement processing is possible, a plurality of intensity receiving antennas may be changed over in the intensity receiving period to measure a plurality of receiving field intensities. For example, as shown in FIG. 29, the receiving field intensity may be sequentially measured at timings t2 and t3 after timing t1, and the receiving field intensity may be sequentially measured at timings t2' and t3' after timing t1'.

Here, the antenna changeover processing procedure will be described with reference to a flowchart shown in FIG. 30. In FIG. 30, the selection controller C8 first detects the connection state of the connector CON1 to CONn based on the signal S6 (step S201). Thereafter, the receiving antenna A1 to An corresponding to the connected connector CON1 to CONn is set as the intensity receiving antenna (step S202). Thereafter, the receiving field intensity of each set intensity receiving antenna is measured (step S203), and an intensity receiving antenna having the largest receiving field intensity is set as the video receiving antenna (step S204). Thereafter, the video signal for one frame is received by the video receiving antenna (step S205).

Thereafter, it is determined whether the connection state of the connector CON1 to CONn has changed (step S206). If the connections state has changed (step S206, YES), the processing proceeds to step S202, where the receiving antenna connected after the change is reset as the intensity receiving antenna and the above processing is repeated. On the other hand, if the connection state has not changed (step S206, NO), the processing proceeds to step S203, where the above processing is repeated to perform the changeover processing to the optimum video receiving antenna.

Figure 31A:
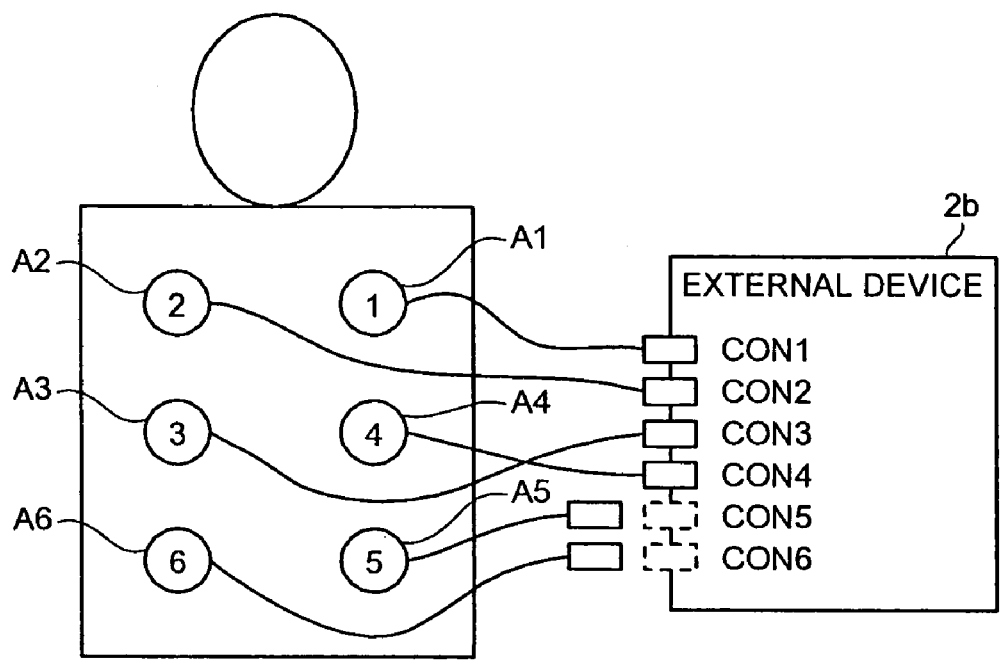
FIGS. 31A and 31B are diagrams showing one example of a connection relationship between receiving antennas and an external device according to the eighth embodiment of the present invention.

For example, there will be considered a case where as shown in FIG. 31A, there are the receiving antennas A1 to A6 corresponding to six arrangement positions "1" to "6", each receiving antenna A1 to A6 comprises the connector CON1 to CON6, respectively, the connectors CON1 to CON4 are connected to the corresponding connecting portions of the connecting unit CON, respectively, and the connectors CON5 and CON6 are not connected thereto. In this case, since it is detected that only the receiving antennas A1 to A4 are connected, the receiving antennas A1 to A4 are set as the intensity receiving antennas, and the video receiving antenna having the largest receiving field intensity is selected from among the receiving antennas A1 to A4.

Figure 31B:
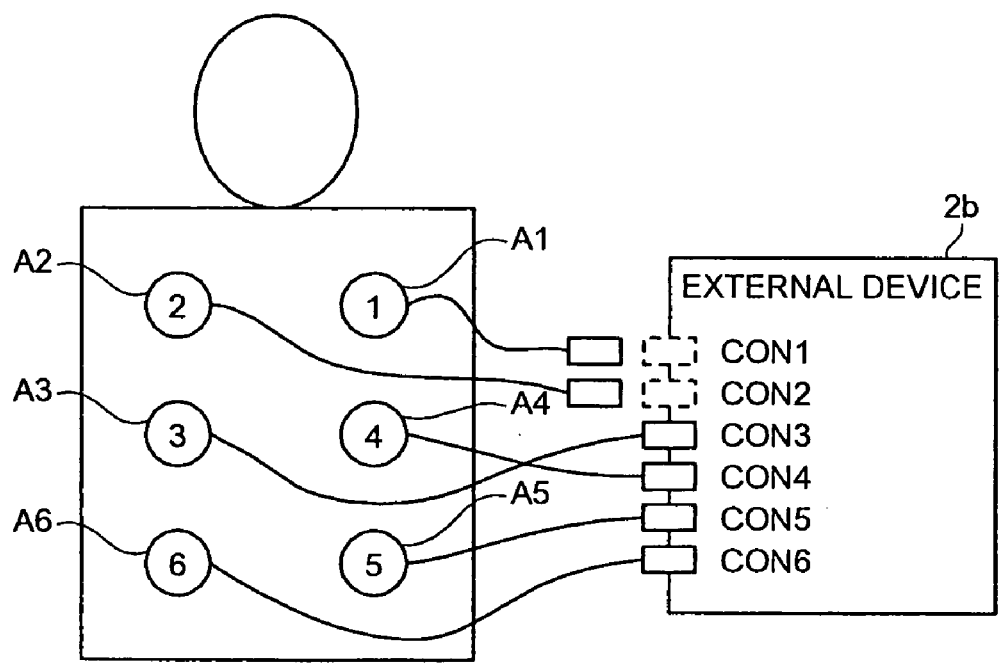

Thereafter, when the connectors CON1 and CON2 are disconnected and the connectors CON5 and CON6 are newly connected as shown in FIG. 31B, the selection controller C1 sets only the receiving antennas A3 to A6 as the intensity receiving antennas, and an intensity receiving antenna having the largest receiving field intensity is selected as the video receiving antenna from among the intensity receiving antennas.

Since the eighth embodiment is constituted so that only the connected receiving antennas A1 to An out of the connector CON1 to CONn are set as the intensity receiving antennas, the time to measure the receiving field intensity for all the intensity receiving antennas is reduced, thereby reducing the time for the antenna changeover processing. Particularly, when only the antenna corresponding to the site to be observed in the body is connected or the number of antennas to be used in a patient having small stature is reduced, it is possible to securely acquire necessary receiving images with simple changeover processing.

A ninth embodiment according to the present invention will now be described. Although the aforementioned eighth embodiment is constituted to comprise all the receiving antennas A1 to An corresponding to the arrangement positions "1" to "6" and to select the intensity receiving antenna based on the presence of the connection with the corresponding connector CON1 to CONn, the ninth embodiment is constituted so that only the receiving antennas necessary for acquiring the antenna receiving field intensity, on which the image receiving and the position calculation of the capsule endoscope 3 are based, are connected to reduce the number of receiving antennas A1 to An so that a reduced number of receiving antennas are reused to efficiently acquire the receiving image and the antenna receiving field intensity. For example, there is constituted so that the antenna at the position unnecessary for the receiving is replaced and reused at a position necessary for the receiving along with the movement of the capsule endoscope 3 in the body.

In other words, the structures of the connectors CON1 to CONn of the receiving antennas A1 to An are made identical and the connector CON1 to CONn is made possible to be connected to the connecting portion of any arrangement position so that a minimum number of receiving antennas are used.

Figure 32A:
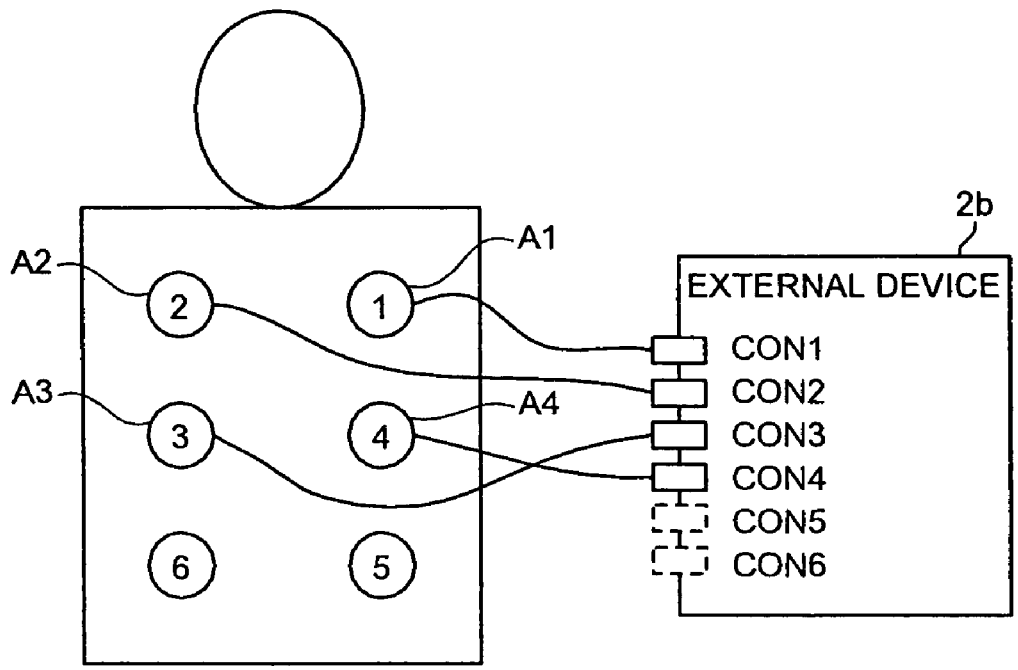
FIGS. 32A and 32B are diagrams showing one example of a connection relationship between receiving antennas and an external device according to a ninth embodiment of the present invention.

As shown in FIG. 32A, the receiving antennas A1 to A4 are arranged at the positions corresponding to the arrangement positions "1" to "4" where the receiving image would be acquired and the connectors CON1 to CON4 are connected to the corresponding connecting portions. Consequently, the receiving antennas A1 to A4 are set as the intensity receiving antennas so that a desired receiving image and the receiving field intensity of each antenna can be obtained by a minimum number of receiving antennas and with simple changeover processing.

Figure 32B:
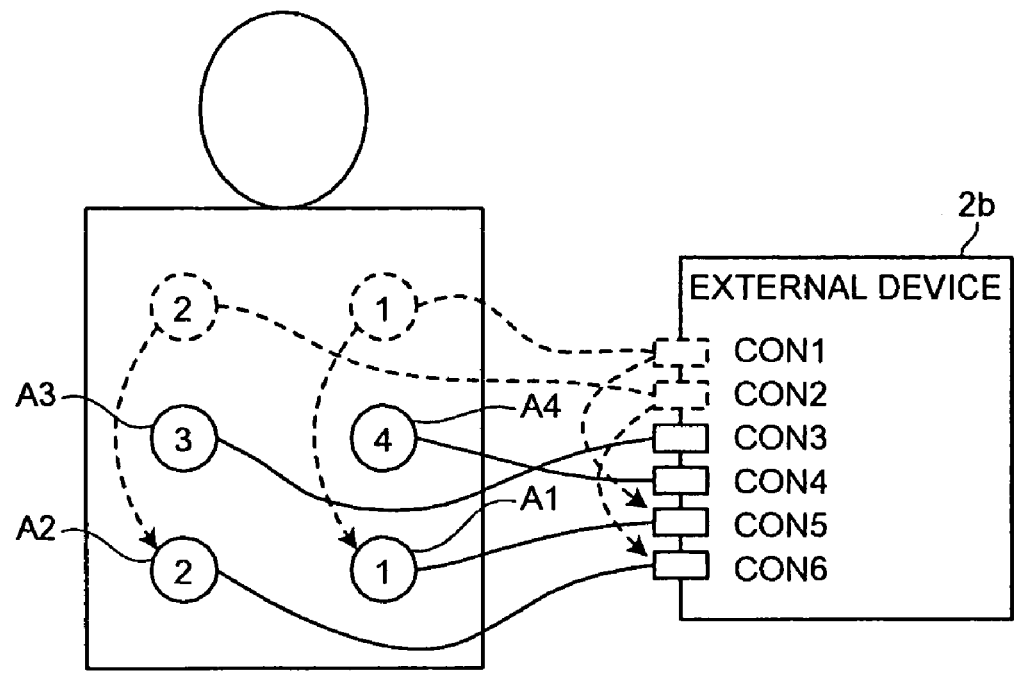

From the arrangement state shown in FIG. 32A, when the receiving images corresponding to other arrangement positions "3" to "6" are to be obtained, aerial portions of the receiving antennas arranged at the arrangement positions "1" and "2" are moved to the portions corresponding to the arrangement positions "5" and "6" and the connectors CON1 and CON2 are instead connected to the connecting portions of the connectors CON5 and CON6, respectively (FIG. 32B). In this manner, the four receiving antennas can be reused to function as the six receiving antennas. Also in this case, the number of intensity receiving antennas is not increased and the changeover processing can be performed by a minimum number of receiving antennas. Further, the time for the intensity receiving antenna changeover processing is reduced, thereby rapidly and securely selecting the optimum video receiving antenna. Furthermore, the number of antennas to be mounted on a patient at one time can be reduced, thereby reducing a load on the patient.

Since the connectors CON1 to CONn correspond to the arrangement positions of the receiving antennas A1 to An in the aforementioned eighth end ninth embodiments, if the connection changes, the changeover information is recorded in correspondence to the receiving image to be used as index information indicating the position of the receiving image.

Since the antenna can be replaced, the antenna at the position unnecessary for the receiving is replaced and reused at a position necessary for the receiving along with the movement of the capsule endoscope in the body, thereby obtaining the necessary receiving image and the antenna receiving field intensity on which the position calculation of the capsule endoscope is based by a small number of antennas.

The structures described in the aforementioned eighth and ninth embodiments are applicable to the aforementioned first to seventh embodiments. In this case, the selection controller C1, C3 to C7 may control as the selection controller C8.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A receiving apparatus for receiving a video signal transmitted as a radio signal from a moving transmitting apparatus by using a plurality of antennas, the receiving apparatus comprising:
   a controller that sequentially changes over each antenna in a vertical blanking period of the video signal added with a dummy signal for receiving intensity measurement in the vertical blanking period to detect a receiving field intensity of the each antenna, and changes to an antenna having the largest receiving field intensity to cause the antenna to receive a video signal other than in the vertical blanking period.

2. The receiving apparatus according to claim 1, wherein the controller measures each receiving field intensity of a plurality of antennas in the vertical blanking period.

3. The receiving apparatus according to claim 1, comprising an antenna changeover unit that is connected to each antenna in correspondence to arrangement positions of the plurality of antennas and detects a connection state of each antenna to change over the connected antennas according to an instruction,
   wherein the controller selects and changes to an antenna whose connection has been detected by the antenna changeover unit.

4. A transmitting apparatus for transmitting an imaged video signal as a radio signal to cause a receiving apparatus having a plurality of antennas to receive the video signal,
   wherein a dummy signal for receiving field intensity measurement, which sequentially changes over each antenna of the receiving apparatus to receive the video signal and detects a receiving field intensity of each antenna, is added and transmitted in a vertical blanking period in the imaged video signal.

5. A transmitting/receiving system including a transmitting apparatus for transmitting an imaged video signal as a radio signal and a receiving apparatus for receiving the video signal by using a plurality of antennas, wherein the transmitting apparatus comprises a dummy signal adder that adds and transmits a dummy signal in a vertical blanking period in the video signal, and the receiving apparatus comprises a controller that sequentially changes over each antenna in the vertical blanking period to detect a receiving field intensity of each antenna from the dummy signal, and changes to an antenna having the largest receiving field intensity to cause the antenna to receive a video signal other than in the vertical blanking period.

6. A receiving apparatus for receiving a radio signal in a frame structure having an information body part including at least information body as a radio signal transmitted from a moving transmitting apparatus and an additional part including information for synchronization by using a plurality of antennas, the receiving apparatus comprising:

a controller that sequentially changes over each antenna in a blank of the radio signal in which a dummy signal for receiving intensity measurement is added in the blank of the information body part whose arrangement position is previously determined to detect a receiving field intensity of each antenna, and changes to an antenna having the largest receiving field intensity to cause the antenna to receive a radio signal of the information body part other than in the blank.

7. The receiving apparatus according to claim 6, wherein the controller sequentially changes over each antenna including part of the additional part to detect a receiving field intensity of the each antenna.

8. The receiving apparatus according to claim 6, wherein the controller measures each receiving field intensity of a plurality of antennas in at least one portion between a blank of the information body part and part of the additional part.

9. The receiving apparatus according to claim 6, wherein the information body part is a video signal, and the blank is a horizontal blanking period.

10. The receiving apparatus according to claim 6, comprising an antenna changeover unit that is connected to each antenna in correspondence to arrangement positions of the plurality of antennas and detects a connection state of each antenna to change over the connected antennas according to an instruction, wherein the controller selects and changes to an antenna whose connection has been detected by the antenna changeover unit.

11. A transmitting apparatus for transmitting an imaged video signal as a radio signal to cause a receiving apparatus having a plurality of antennas to receive the video signal, wherein each antenna of the receiving apparatus is sequentially changed and received in a horizontal blanking period in the video signal to add and transmit a dummy signal for receiving field intensity measurement for detecting a receiving field intensity of each antenna.

12. A transmitting/receiving system including a transmitting apparatus for transmitting an imaged video signal as a radio signal and a receiving apparatus for receiving the video signal by using a plurality of antennas, wherein the transmitting apparatus comprises a dummy signal adder that adds and transmits a dummy signal in a horizontal blanking period in the video signal, and the receiving apparatus comprises a controller that sequentially changes over each antenna in the horizontal blanking period to detect a receiving field intensity of the each antenna from the dummy signal, and changes to an antenna having the largest receiving field intensity to cause the antenna to receive a video signal other than in the horizontal blanking period.

13. The transmitting/receiving system according to claim 12, wherein the controller sequentially changes over each antenna including a synchronization signal period for receiving field intensity measurement added to the video signal to detect a receiving field intensity.

* * * * *